US012411135B2

(12) United States Patent
Ban et al.

(10) Patent No.: US 12,411,135 B2
(45) Date of Patent: Sep. 9, 2025

(54) METHODS AND DEVICES FOR DETECTING A PATHOGEN AND ITS MOLECULAR COMPONENTS

(71) Applicant: THE REGENTS OF THE UNVERSITY OF CALIFORNIA, Oakland, CA (US)

(72) Inventors: Deependra Kumar Ban, San Diego, CA (US); Ratnesh Lal, La Jolla, CA (US); Gennadi Glinskii, La Jolla, CA (US); Prabhakar R. Bandaru, San Diego, CA (US); Sunil Srivastava, La Jolla, CA (US); Scott John, Los Angeles, CA (US); Tyler Bodily, La Jolla, CA (US); Abhijith Karkisaval Ganapati, La Jolla, CA (US)

( * ) Notice: Subject to any disclaimer, the term of this patent is extended or adjusted under 35 U.S.C. 154(b) by 0 days.

(21) Appl. No.: 18/623,934

(22) Filed: Apr. 1, 2024

(65) Prior Publication Data
US 2024/0393327 A1 Nov. 28, 2024

Related U.S. Application Data

(63) Continuation of application No. 17/649,554, filed on Jan. 31, 2022, now Pat. No. 11,946,931.
(Continued)

(51) Int. Cl.
*G01N 33/543* (2006.01)
*C12Q 1/68* (2018.01)
(Continued)

(52) U.S. Cl.
CPC .......... *G01N 33/5438* (2013.01); *C12Q 1/68* (2013.01); *C12Q 1/6816* (2013.01); *G01N 27/00* (2013.01);
(Continued)

(58) Field of Classification Search
CPC ......... G01N 33/5438; G01N 33/56983; G01N 27/00; G01N 2333/165; C12Q 1/68; C12Q 1/6816; H01L 2924/1306
See application file for complete search history.

(56) References Cited

U.S. PATENT DOCUMENTS 10,793,898 B2  10/2020  Lal et al.
2014/0080198 A1  3/2014  Lal et al.
(Continued)

OTHER PUBLICATIONS

Seo, Giwan, et al. "Rapid detection of COVID-19 causative virus (SARS-COV-2) in human nasopharyngeal swab specimens using field-effect transistor-based biosensor." ACS nano 14.4 (2020): 5135-5142. (Year: 2020).*
(Continued)

*Primary Examiner* — Robert J Eom
(74) *Attorney, Agent, or Firm* — Perkins Coie LLP

(57) ABSTRACT

Methods, systems and devices for detecting the presence of a pathogen, for example, a virus (e.g., SARS-COV-2), or its molecular components, in health care-related samples and/or environmental samples are disclosed. An example system for improving detection of a pathogen includes biosensor device comprising a detection chip and at least one probe that specifically recognizes a pathogen, where the detection chip comprises a graphene field-effect transistor (FET) chip and the probe, which comprises an aptamer, specifically binds to a DNA, RNA, or protein associated with the pathogen.

20 Claims, 26 Drawing Sheets
Specification includes a Sequence Listing.

Related U.S. Application Data

(60) Provisional application No. 63/144,460, filed on Feb. 1, 2021.

(51) Int. Cl.
   *C12Q 1/6816* (2018.01)
   *G01N 27/00* (2006.01)
   *G01N 33/569* (2006.01)

(52) U.S. Cl.
   CPC . *G01N 33/56983* (2013.01); *G01N 2333/165* (2013.01); *H01L 2924/1306* (2013.01)

(56) References Cited

U.S. PATENT DOCUMENTS

| | | |
|---|---|---|
| 2014/0162390 A1 | 6/2014 | Afzali-ardakani et al. |
| 2017/0350856 A1 | 12/2017 | Kobayashi et al. |
| 2019/0256897 A1 | 8/2019 | Lal et al. |
| 2019/0376926 A1 | 12/2019 | Tarasov |
| 2021/0293816 A1 | 9/2021 | Nawana et al. |
| 2022/0011293 A1 | 1/2022 | Hummer et al. |

OTHER PUBLICATIONS

Ban, D. et al. "Direct DNA Methylation Profiling with an Electric Biosensor" ACS Nano; 2020; vol. 14, No. 6, pp. 6743-6751.

Hwang, M. et al. "DNA Nano-tweezers and Graphene Transistor Enable Label-free Genotyping" Advanced Materials; 2018; 16 pages.

Hwang, M. et al. "Highly specific SNP detection using 2D graphene electronics and DNA strand displacement" PNAS; 2016; vol. 113; No. 26; pp. 7088-7093.

ISA, International Search Report and Written Opinion for PCT Application No. PCT/US2022/070448. Mail Date: Apr. 1, 2022. 16 pages.

Daniloski, Zharko, et al., "The Spike D614G mutation increases SARS-CoV-2 infection of multiple human cell types", eLife 2021, 10, e65365, pp. 1-16.

De Oliveira Andrade, Rodrigo , "Covid-19 is causing the collapse of Brazil's national health service", BMJ 2020, 370, 2 pp.

Ding, Zhao, "Galectin-1-induced Skeletal Muscle Cell Differentiation of Mesenchymal Stem Cells Seeded on an Acellular Dermal Matrix Improves Injured Anal Sphincter", Discovery Medicine, May 22, 2016, pp. 1-9.

Garcia-Beltran, Wilfredo F, et al., "Multiple SARS-CoV-2 variants escape neutralization by vaccine-induced humoral immunity", Cell 2021, 184, 2372, 2021, 24 pp.

Guo, Shuxin, et al., "The Genetic Variant of SARS-CoV-2: would It Matter for Controlling the Devastating Pandemic?", Int J Biol Sci 2021, 17, 1476, pp. 1476-1485.

Khan, Suliman, et al., "COVID-19: Clinical aspects and therapeutics responses", Saudi Pharmaceutical Journal 2020, 28, 1004, pp. 1004-1008.

Pan, Xingfei, et al., "", Viral load of SARS-CoV-2 in clinical samples, vol. 20, Apr. 2020, www.thelancet.com/infection.

Plante, Jessica A, et al., "Spike mutation D614G alters SARS-CoV-2 fitness", Nature 2021, 592, 116, Apr. 2021, pp. 116-137.

Pollock, Nira R., et al., "Correlation of SARS-CoV-2 Nucleocapsid Antigen and RNA Concentrations in Nasopharyngeal Samples from Children and Adults Using an Ultrasensitive and Quantitative Antigen Assay", Journal of Clinical Microbiology, Apr. 2021, vol. 59, Issue 4 e03077-20, 1-10.

Romani, Lorenza, et al., "Gut Mucosal and Fecal Microbiota Profiling Combined to Intestinal Immune System in Neonates Affected by Intestinal Ischemic Injuries", Frontiers in Cellular and Infection Microbiology 2020, 10, 724, 9 pp.

Ross, Georgina M.S, et al., "Unravelling the Hook Effect: A Comprehensive Study of High Antigen Concentration Effects in Sandwich Lateral Flow Immunoassays", Anal. Chem. 2020, 92, 15587, 2020, pp. 15587-15595.

Song, Yanling, et al., "Discovery of Aptamers Targeting the Receptor-Binding Domain of the SARS-CoV-2 Spike Glycoprotein", Analytical Chemistry 2020, 92, 9895, pp. 9895-9900.

Sorbello, M., et al., "The Italian coronavirus disease 2019 outbreak: recommendations from clinical practice", Anaesthesia 2020, 75, 724-732.

Tai, W., et al., "Characterization of the receptor-binding domain (RBD) of 2019 novel coronavirus: implication for development of RBD protein as a viral attachment inhibitor and vaccine", Cellular & Molecular Immunology 2020, 17, 613, pp. 613-620.

Wang, Mei-Yu, et al., "SARS-CoV-2: Structure, Biology, and Structure-Based Therapeutics Development", Frontiers in Cellular and Infection Microbiology, Nov. 2020, vol. 10 Article 587269, 1-17.

Winder, Abigail D, et al., "The "hook effect" causing a negative pregnancy test in a patient with an advanced molar pregnancy", Gynecol Oncol Rep 2017, 21, 34, 2017, pp. 34-36.

Zhang, Liyun, et al., "Discovery of sandwich type COVID-19 nucleocapsid protein DNA aptamers", Chemical Communications 2020, 56, 10235, pp. 10235-10238.

Zhang, Lizhou, et al., "The D614G mutation in the SARS-CoV-2 spike protein reduces S1 shedding and increases infectivity", bioRxiv 2020, 2020.06.12.148726, 25 pp.

N. Miyakawa et al., "Drift Suppression of Solution-Gated Graphene Field-Effect Transistors by Cation Doping for Sensing Platforms," Sensors 21, 7455 (2021), 11 pages.

EPO, Extended European Search Report for European Application No. 22746929.3, mailed on Jan. 3, 2025, 9 pages.

Seo, G. et al., "Rapid Detection of COVID-19 Causative Virus (SARS-CoV-2) in Human Nasopharyngeal Swab Specimens Using Field-Effect Transistor-Based Biosensor," ACS Nano, vol. 14, No. 4, Apr. 2020, 9 pages.

Sengupta, J. et al., "Graphene-based field-effect transistor biosensors for the rapid detection and analysis of viruses: A perspective in view of COVID-19," Carbon Trends, vol. 2, Jan. 2021, pp. 1-8.

Wu, G. et al., "Graphene Field-Effect Transistors for the Sensitive and Selective Detection of Escherichia coli Using Pyrene-Tagged DNA Aptamer," Advanced Healthcare Materials, vol. 6, No. 19, Oct. 2017, pp. 1-9.

Wang, X. et al., " Measurements of aptamer-protein binding kinetics using graphene field-effect transistors," Nanoscale, vol. 11, No. 26, Jan. 2019, pp. 12573-12581.

Wang, Z. et al., "A Flexible and Regenerative Aptameric Graphene-Nafion Biosensor for Cytokine Storm Biomarker Monitoring in Undiluted Biofluids toward Wearable Applications," Advanced Functional Materials, vol. 31, No. 4, Sep. 2020, pp. 1-10.

\* cited by examiner

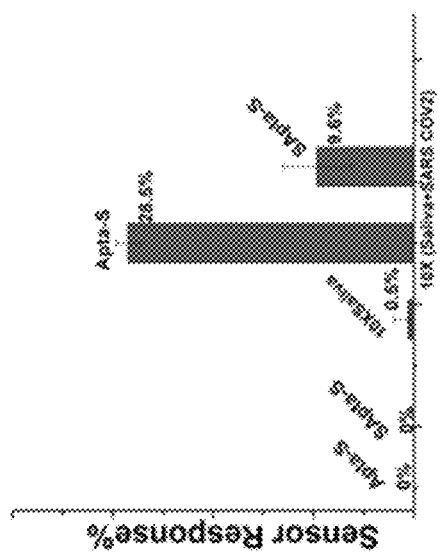
FIG. 19A
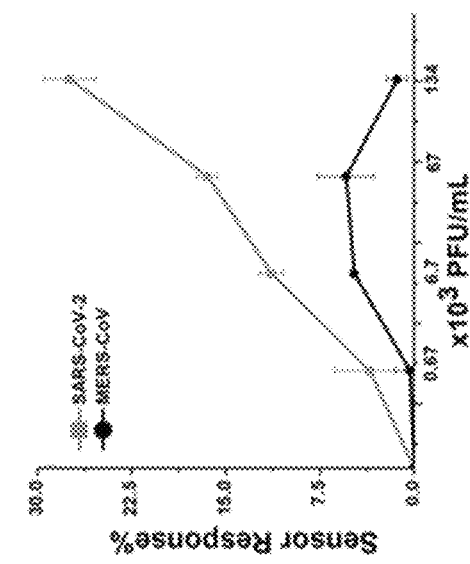
FIG. 19B
FIG. 19C
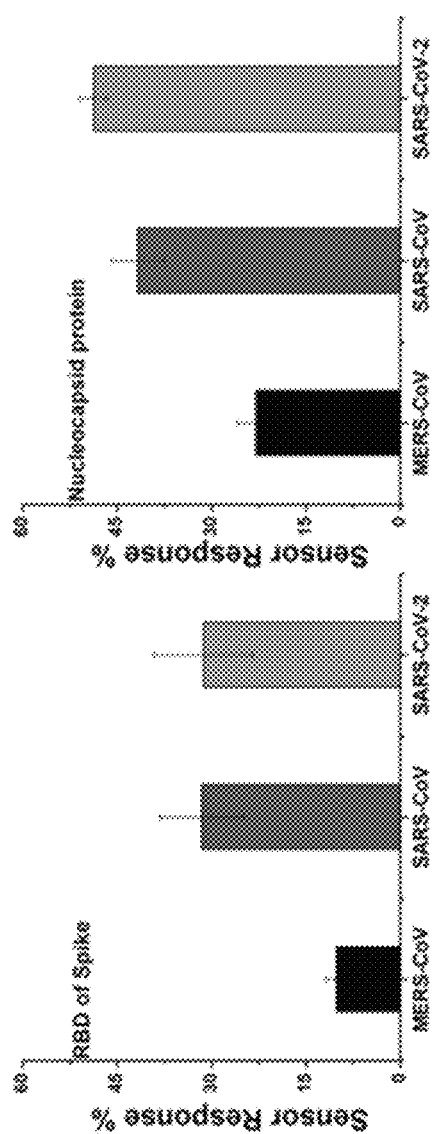
FIG. 19D
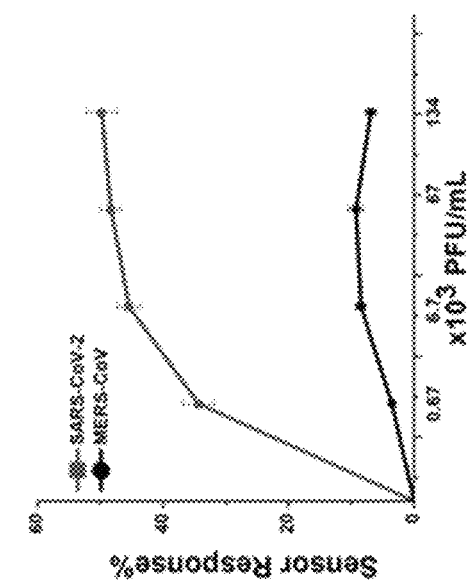
FIG. 19E
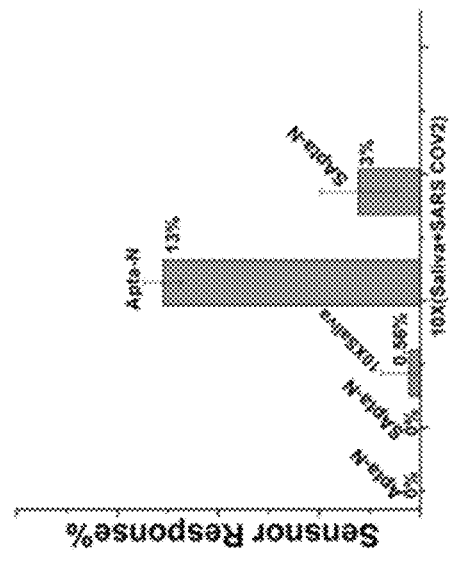
FIG. 19F

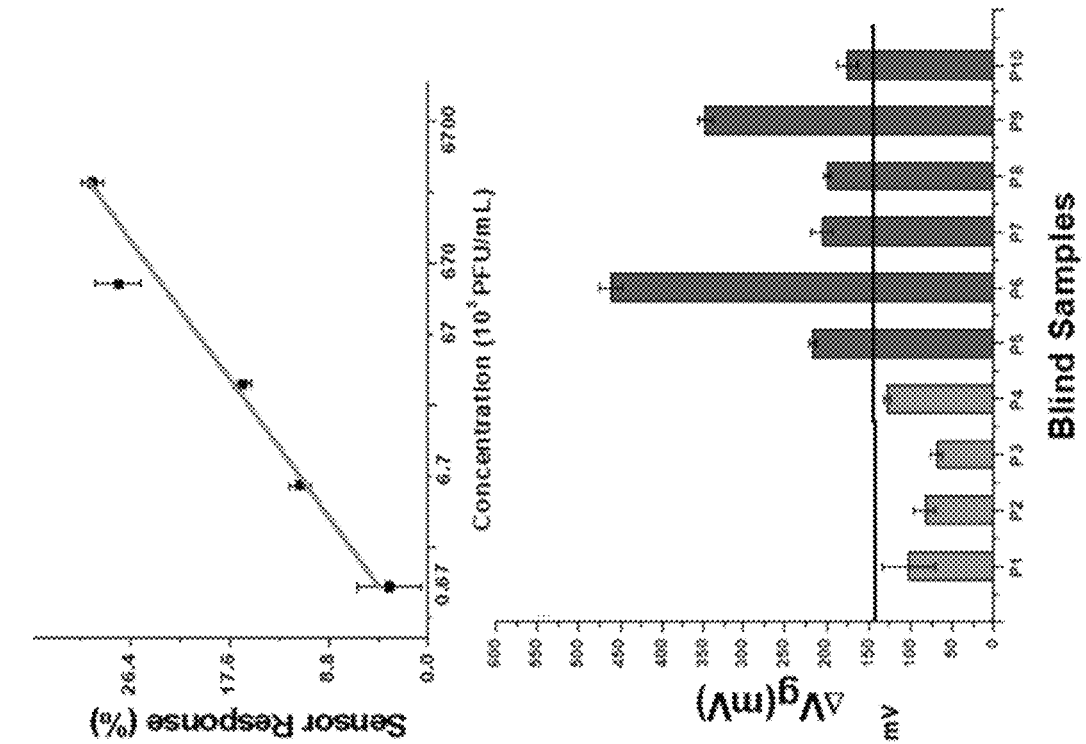
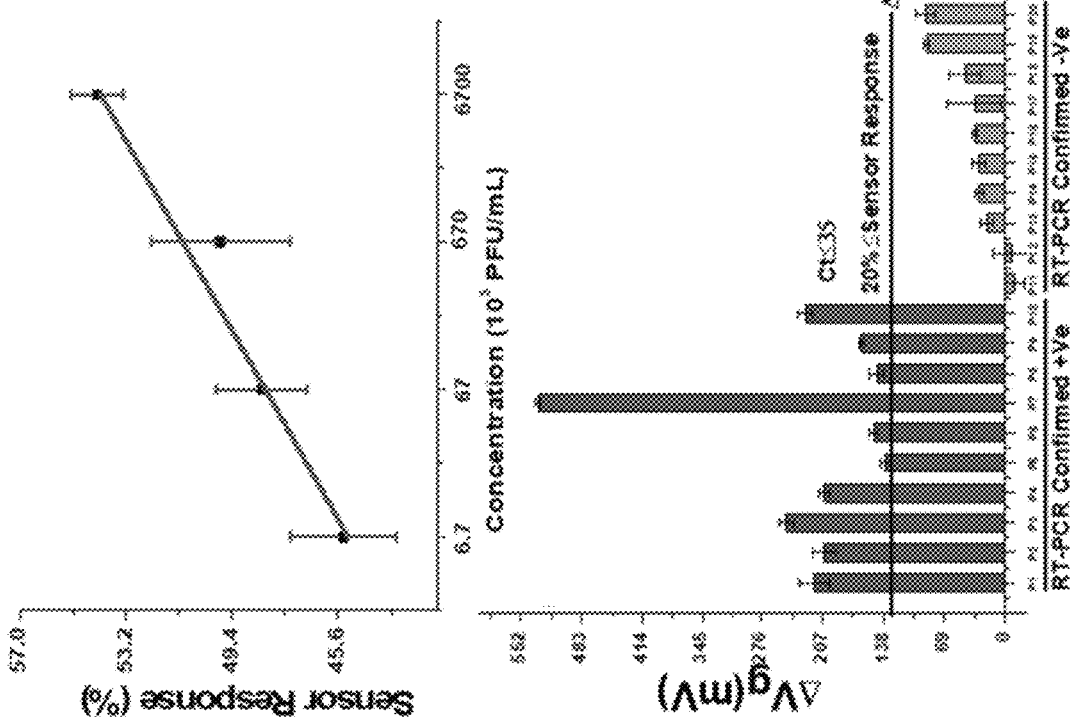
FIG. 20A  FIG. 20B  FIG. 20C  FIG. 20D

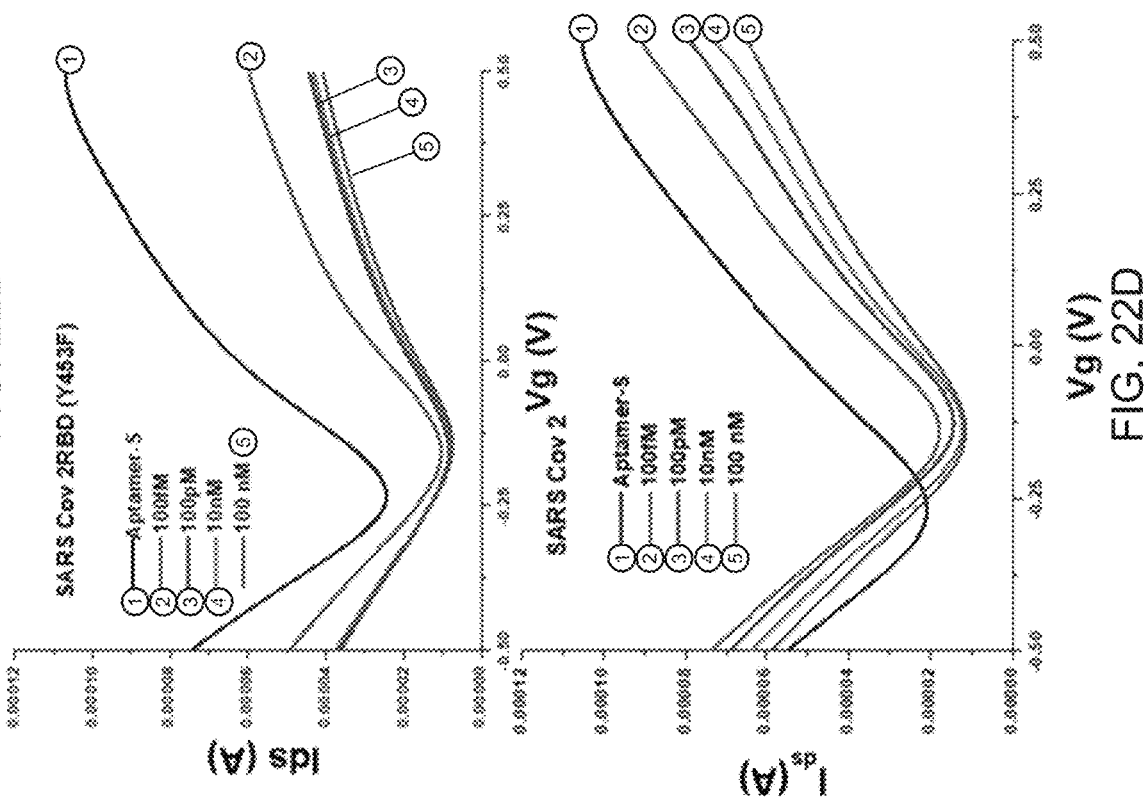
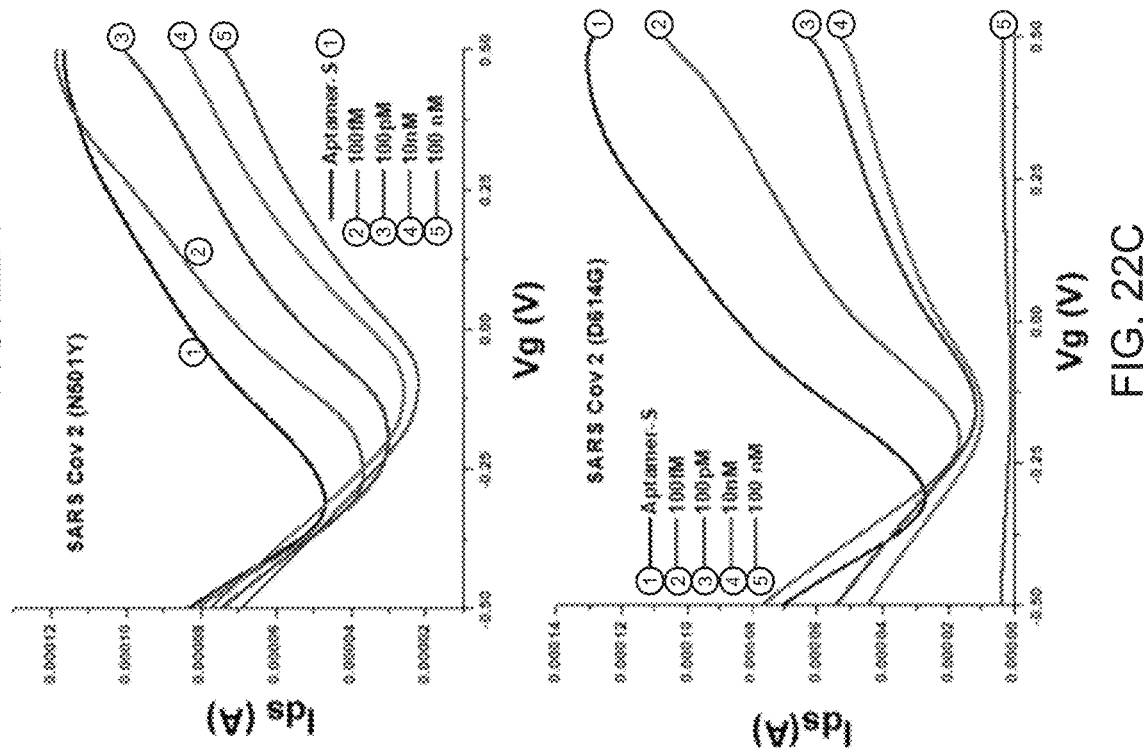
FIG. 22A  FIG. 22B  FIG. 22C  FIG. 22D

SEQUENCE LISTING

```
Sequence total quantity: 8
SEQ ID NO: 1            moltype = DNA  length = 51
FEATURE                 Location/Qualifiers
misc_feature            1..51
                        note = Synthetic: Aptamer-S
source                  1..51
                        mol_type = other DNA
                        organism = synthetic construct
SEQUENCE: 1
cagcaccgac cttgtgcttt gggagtgctg gtccaagggc gttaatggac a          51

SEQ ID NO: 2            moltype = DNA  length = 67
FEATURE                 Location/Qualifiers
misc_feature            1..67
                        note = Synthetic: Aptamer-S1
source                  1..67
                        mol_type = other DNA
                        organism = synthetic construct
SEQUENCE: 2
atccagagtg acgcagcatt tcatcgggtc caaaaggggc tgctcgggat tgcggatatg  60
gacacgt                                                           67

SEQ ID NO: 3            moltype = DNA  length = 58
FEATURE                 Location/Qualifiers
misc_feature            1..58
                        note = Synthetic: Aptamer-N
source                  1..58
                        mol_type = other DNA
                        organism = synthetic construct
SEQUENCE: 3
gctggatgtc gcttacgaca atattcctta ggggcaccgc tacattgaca catccagc    58

SEQ ID NO: 4            moltype = DNA  length = 58
FEATURE                 Location/Qualifiers
misc_feature            1..58
                        note = Synthetic: Aptamer-N1
source                  1..58
                        mol_type = other DNA
                        organism = synthetic construct
SEQUENCE: 4
gctggatgtc accggattgt cggacatcgg attgtctgag tcatatgaca catccagc    58

SEQ ID NO: 5            moltype = RNA  length = 85
```

```
FEATURE             Location/Qualifiers
misc_feature        1..85
                    note = Synthetic: Aptamer-N2
source              1..85
                    mol_type = other RNA
                    organism = synthetic construct
SEQUENCE: 5
gggagagcgg aagcgtgctg ggcctgtcgt tcgctgtgtc ttgctacgtt acgttacacg    60
gttggcataa cccagaggtc gatgg                                         85

SEQ ID NO: 6        moltype = RNA  length = 84
FEATURE             Location/Qualifiers
misc_feature        1..84
                    note = Synthetic: Aptamer-N3
source              1..84
                    mol_type = other RNA
                    organism = synthetic construct
SEQUENCE: 6
gggagagcgg aagcgtgctg ggcctcatta cacacatctc acgggagaca tagctgacga    60
tatccataac ccagaggtcg atgg                                           84

SEQ ID NO: 7        moltype = DNA  length = 51
FEATURE             Location/Qualifiers
misc_feature        1..51
                    note = Synthetic: Scrambled Aptamer-S
source              1..51
                    mol_type = other DNA
                    organism = synthetic construct
SEQUENCE: 7
ggtggtttga ctgatcagag actatgcagc tctggcccgc tagccggaag t             51

SEQ ID NO: 8        moltype = DNA  length = 58
FEATURE             Location/Qualifiers
misc_feature        1..58
                    note = Synthetic: Scrambled Aptamer-N
source              1..58
                    mol_type = other DNA
                    organism = synthetic construct
SEQUENCE: 8
taggtatatg tacgcacacc taagtcagct tgcccgacgc tgcagctcac atgtatgc      58
```

METHODS AND DEVICES FOR DETECTING A PATHOGEN AND ITS MOLECULAR COMPONENTS

CROSS-REFERENCE TO RELATED APPLICATION

This patent document is a continuation of U.S. application Ser. No. 17/649,554 filed on Jan. 31, 2022, which claims priority to and benefits of U.S. Provisional Application No. 63/144,460, entitled "METHOD AND DEVICE FOR DETECTION OF A VIRUS AND ITS MOLECULAR COMPONENTS," and filed on Feb. 1, 2021. The entire content of the before-mentioned patent application is incorporated by reference as part of the disclosure of this patent document.

STATEMENT REGARDING FEDERALLY SPONSORED RESEARCH

This invention was made with government support under Grant No. HL119893 awarded by the National Institutes of Health. The government has certain rights in the invention.

REFERENCE TO SEQUENCE LISTING SUBMITTED VIA EFS-WEB

This patent document contains an ST.26 compliant Sequence Listing, which is submitted concurrently in xml format via Patent Center and is hereby incorporated by reference in its entirety. The .xml copy, created on Feb. 19, 2025, is named 0090628446US02 Sequence Listing.xml and is 11,610 bytes in size.

TECHNICAL FIELD

This patent document generally relates to detection of pathogens, and more specifically, to using field-effect transistors and aptamers to accurately detect a virus and its molecular components.

BACKGROUND

Pathogens such as viruses and bacteria pose a significant concern for human health. For example, coronaviruses are a large family of RNA viruses that may cause upper-respiratory tract diseases in humans that range from mild to lethal in severity. The most recent novel coronavirus to cause worldwide pandemic and health care crises is SARS-COV-2, which causes coronavirus disease 2019 (COVID-19). SARS-COV-2 emerged in December 2019 and was declared a global pandemic by the World Health Organization (WHO) on Mar. 11, 2020. According to recent report, COVID-19 is highly contagious (>96 million positive cases) and causes a high morbidity rate (>2 million death) worldwide.

To successfully combat the pandemic, coordinated implementation of multiple population-scale health care measures is required. One of the cornerstones of this multi-probe strategy is everyday real-time access to reliable, fast, inexpensive at-home, workplaces, and point-of-care (POC) diagnostic tests which would be carried out on simple in use diagnostic devices with wireless data transmission capabilities for continuing pandemic monitoring. Despite tremendous effort in this area, no such methodologies and devices exist.

SUMMARY

The disclosed technology relates to methods, systems, and devices for detecting the presence of a pathogen, for example, a virus (e.g., SARS-COV-2), or its molecular components in health care-related samples and/or environmental samples.

In some example aspects, a biosensor device is provided to detect the presence of at least a finite count/amount of a viral particle, RNA, DNA, or protein associated with a pathogen of interest, for example, the SARS-COV-2 virus. However, the specificity of the biosensor can be advantageously changed to detect biological pathogens other than viruses, e.g., flu, bacteria, toxins, or fungi. Thus, embodiments of the disclosed technology can be deployed in efforts that range from global heath to global security.

In other example aspects, the biosensor device comprises a detection chip, for example, a graphene field-effect transistor (FET) chip. In some embodiments, the detection chip comprises a probe attached to the detection chip, for example, an aptamer, that specifically binds to a target the viral antigen, particle, RNA, DNA, or protein. In some embodiments, the aptamer is an oligonucleotide (RNA or DNA, single-stranded or double-stranded). In some embodiments, the aptamer is a peptide.

In yet other example aspects, methods are provided for detecting whether a subject has been exposed to a particular virus, for example, the SARS-COV-2 virus, by using the biosensor device of the present technology to detect the presence of the viral particle, RNA, DNAs, or protein associated with the virus in a sample from the subject.

In yet other example aspects, devices biosensor devices are provided for detecting one or more pathogens. In an example, the biosensor device includes a detection chip, which includes (a) a substrate with a graphene surface, (b) a conducting material at a first end and a second end of the graphene surface that form a first electrode and a second electrode, respectively, and (c) an insulating material to insulate the first electrode and the second electrode. In this example, one or more probes, which are attached to the graphene surface, specifically bind to one or more target molecules of the one or more pathogens. Furthermore, the insulating material forms a well to receive a biological sample such that the biological sample is in contact with the one or more probes.

BRIEF DESCRIPTION OF THE DRAWINGS

FIG. 14-17 show examples of detection of SARS-COV-2 using aptamers specific to viral proteins with high specificity and sensitivity.

FIGS. 19A-19F show example results for sensor specificity based on testing aptamer-S and -N by using closely correlated cognate antigens of MERS-COV, SARS-COV and inactive MERS-COV virus.

FIGS. 20A and 20B show examples results for a concentration dependent sensor response with different concentrations of inactive viruses and 10% saliva for the Aptamer-S derivatized GFET and the Aptamer-N derivatized GFET, respectively.

FIG. 20C shows results of oral swab samples of RT-PCR positive and negative tests corresponding to point-of-care (POC) antigen tests from the FDA EUA.

FIG. 20D shows results of a blind sample test using the Aptamer-S derivatized graphene FET.

FIGS. 22A-22C show examples of detecting the SARS-COV-2 RBD cognate protein of mutant viruses.

FIG. 22D shows an example of detecting the SARS-COV-2 RBD cognate protein of the original virus.

DETAILED DESCRIPTION

Figure 1A:
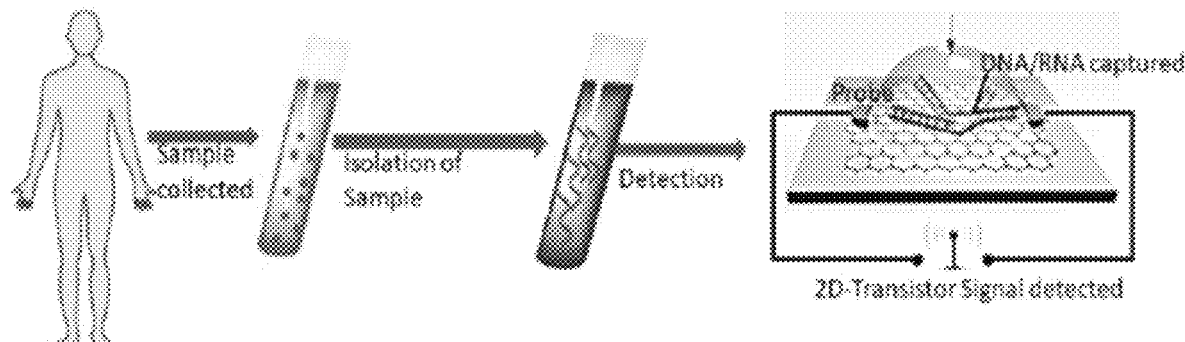
FIGS. 1A-1C and 2A-2C are schematics showing the design and mechanism of a portable chip-based electronic biosensor device with a wireless communication module that facilitates efficient detection of viral RNA/DNA targets and surveillance of the viral pandemic, in accordance with the presently disclosed technology.
Figure 1B:
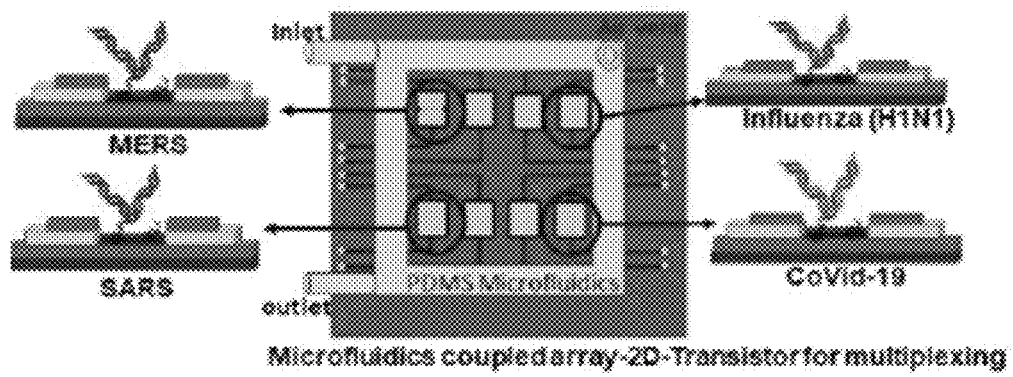
Figure 1C:
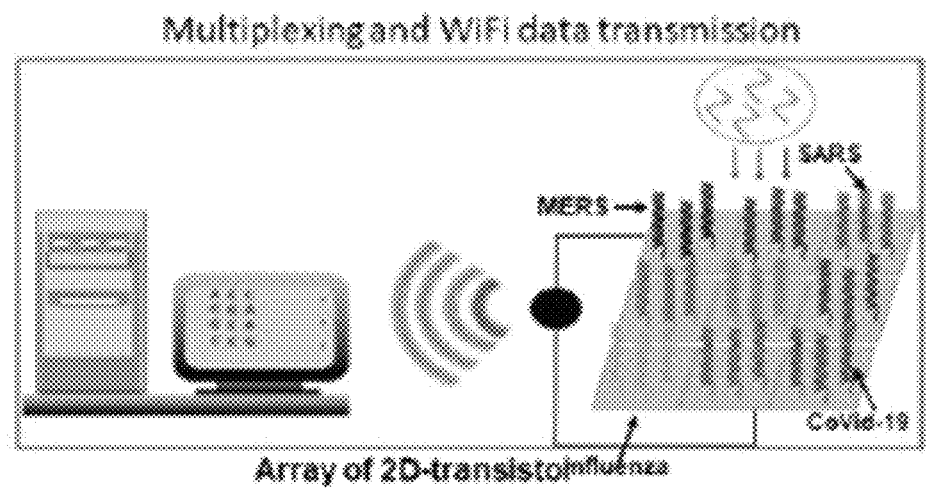

Disclosed are methods, devices and systems that pertain to the detection of proteins, nucleic acids, and viruses and/or other pathogens such as bacteria, fungi, or biological toxins. In particular, disclosed are a portable wireless electronic biosensor device comprising a biosensor chip for the detection of a pathogen (e.g., a virus like SARS-COV-2) or its molecular components from a biological sample, e.g., a sample of bodily fluid (e.g., saliva, sweat, tears, exhaled breath, blood, urine) from a person, nasal, nasopharyngeal, or fecal swabs of a person, or in environmental samples, e.g., air, water, air borne pathogens, and household and industrial waste. The hand-held, self-contained, portable, diagnostic device incorporates wireless communication technology and allows highly specific and sensitive pathogen detection with results reported within minutes. The described embodiments advantageously enable rapid and precise identification of SARS-CoV-2 and potentially other emerging viral antigens around the world.

EXAMPLE EMBODIMENTS IN GLOBAL HEALTH APPLICATIONS

A person infected with a pathogen, for example the SARS-COV-2 virus, may eject the virus or tiny aerosolized droplets containing the virus by coughing, speaking, or otherwise exhaling breath. A person's saliva may also contain measurable levels of the virus. A device comprising a detection chip indicating the presence of a target protein or nucleic acid associated with a particular virus, for example the SARS-COV-2 virus, could therefore be breathed onto or into by a user, or a droplet of saliva from the user could be deposited into the device to test the user for the presence of the SARS-COV-2 virus. Such a device capable of signaling the presence of the SARS-COV-2 virus would benefit from being portable and reusable for the testing of multiple persons. However, a reusable device would necessitate a careful distinction between reusable and disposable portions of the device such as, for example a mouthpiece disposed to contact the mouth of a user, to prevent inadvertent infection of uninfected users via using a contaminated device.

Amidst a global pandemic associated with SARS-COV-2 virus, and the risk of similar emerging outbreaks, or even mutations thereof, there exists a need to quickly, safely, and easily test people for the likely presence or absence of the SARS-COV-2 virus, or other viruses related to disease. It would be beneficial to be able to test people to assess the presence or absence of a disease related virus in their breath or saliva with minimal delay and risk of transmission between persons. For example, it would be beneficial to quickly, safely, and easily test people within a given population sample or location that may include for example without limitation, an airport, a library, a theater, a classroom, a restaurant or bar, an office setting or lobby, a hotel or inn lobby/intake, places of public transportation, hospital/urgent care/doctor's offices, or any other internal space where people may gather and where transmission of the virus between persons is possible.

Furthermore, the portability of the described embodiments would enable the biosensor devices to be deployed in areas that may be ascertained as sources of the pathogens, e.g., caves in the example of SARS-COV-2. This efficacy of the deployment is bolstered by the wireless connectivity and capabilities of the biosensor device, which would be able to periodically update research and medical facilities, and the sensitivity of the graphene FET, which would be able to detect very low concentrations of the pathogen, thereby enabling early detection at the source.

EXAMPLE EMBODIMENTS IN GLOBAL SECURITY APPLICATIONS

Biological threats. Biological threats can emerge without warning from nature, deliberate attacks, or accidental release. Infectious diseases that sweep the world, e.g., MERS-COV and SARS-COV-2 as discussed above, pathogens that are accidentally released from research laboratories, including from laboratories working on non-circulating viruses, e.g., smallpox, or from research work that has created novel epidemic strains of pathogens, can only be brought under control after enormous international collaboration with governments in the region that have been affected and many billions of dollars spent. Inter-connected travel and commerce, especially from regions in which the pathogens have originated, quickly result in the spread of a pathogen all over the world.

Governments have frequently relied on the private sector to make the vaccines, medicines, diagnostics and medical equipment etc. that are needed to respond upon the emergence of biological threats. Embodiments of the disclosed technology would be critical in the establishment of national and sub-national monitoring systems that can predict and identify infectious disease threats. The sensitivity of the graphene FET, which enables detection of very low concentrations, and the portability and cost-effectiveness of the described biosensor devices can be leveraged in deployments that can serve as large-scale early warning systems for biological threats.

Environmental monitoring. The ability to deploy the described biosensor devices on a large-scale make them well suited for environmental monitoring, and in particular, for the detection of environmental contaminants such as heavy metals, small-molecule agricultural toxins, and water-borne bacterial pathogens. Additional targets include aquatic toxins, pesticides, industrial byproducts, antibiotics, and pharmaceuticals. Traditional multi-step detection processes may degrade many environmental contaminants of interest, which may already be at low concentrations. Embodiments of the disclosed technology provide on-site detection and the dissemination of results via built-in wireless capabilities, which make the described aptamer-based biosensors particularly useful for monitoring water, soil, and air.

Advantages and Benefits of the Disclosed Technology

Therefore, there exists a need for a device that can test for a plurality of disease-related pathogens via a single test. It would be beneficial for such a device to be hand-held, self-contained, and portable, with a known test result generated within minutes of testing. It would be further beneficial for such tests to be cost-effective and the results to be immediately transmitted to non-technical personnel as well as doctors, administrators, and public health individuals. Such a device would further benefit from the ability to test positive for variants of pathogens, which allow for diagnosing potential future mutations of known virus genomes, for example the SARS-COV-2 genome, using aptamers or nucleic acids against such variants.

Embodiments of the disclosed technology employ graphene FET-biosensor chips, which have been used in conjunction with double-stranded probes for detecting nucleotide acids with a single nucleotide resolution via strand displacement (e.g., see U.S. Pat. No. 10,793,898 that discloses graphene field-effect transistor (FET)-based electrical biosensor chips). Compared with optical sensors, electrical biosensors have higher (Atto-Pico molar) specificity and thus reduces the need for sample amplification. FET-based sensors, in particular, can sense change in electric charges during biomolecular interactions and affords highest possible sensitivity as every atom on the surface is used, i.e., single electron charge sensitivity. Electrical biosensors also allow faster read-outs, low power consumption, portability, inexpensive mass production, integrated sensor and measurement systems, and no labeling of biomolecules.

However, compared with known double-stranded nucleic acid probe and chip-based devices, the present technology has extended and superior capabilities, including the use of single stranded aptamers as probes, the detection of the electrical current resulting from simple probe-sample interactions, and the ability to design aptamers specific to nucleic acid targets as well as proteins of interest (e.g., spike proteins of SARS-COV-2). These features allow for versatility in the application of aptamers for nucleic acids, protein, and other sensing needs, making the current technology simpler and tunable.

Embodiments of the disclosed technology provide, amongst other features and benefits, the following distinct advantages:

(1) Aptamers, selected from amongst thousands of available aptamers, that are able to bind to specific proteins;

(2) Aptamers that retain their specificity even when attached to a solid; and (3) Aptamers that can recognize mutations of a pathogen.

Publicly available aptamer databases, e.g., Apta-index by Aptagen, contain sequences drawn from hundreds of published experiments. Entries in the database typically provide detailed, structured information about the experimental conditions under which aptamers were selected and their binding affinity quantified. A variety of analytical techniques have been employed to identify the best candidates that bind to the specific proteins considered herein, and embodiments of the disclosed technology use these aptamers to detect, with high sensitivity and specificity, various pathogens.

Existing implementations that use aptamers have always used aptamers in solution to detect pathogens. A common limitation of aptamer-based assays has always been the possible drastic changes in their binding properties due to their immobilization on solid substrates. However, the described embodiments attach the aptamers to graphene surfaces with the aptamers unexpectedly retaining their specificity, and can thus be incorporated into an electrical/electronic detection framework with high sensitivity. Prior art systems that used aptamers in solution could not teach or suggest immobilizing aptamers on a solid graphene surface as described in disclosed technology.

The described embodiments use aptamers (or equivalent, DNA), instead of antibodies, to bind to specific proteins. Thus, the inherent disadvantage of antibodies in detecting mutations is circumvented by using aptamers. As is evidenced from the results presented in this patent document, the SARS-COV-2 virus, as well as its Omicron and Delta variants, are detected accurately using the aptamer-based GFET devices that exhibit high specificity and high sensitivity.

While the present disclosure is capable of being embodied in various forms, the description below of several embodiments is made with the understanding that the present disclosure is to be considered as an exemplification of the invention and is not intended to limit the invention to the specific embodiments illustrated.

Section headings are used in the present document to improve readability of the description and do not in any way limit the discussion or the embodiments (and/or implementations) to the respective sections only.

Examples of Detection Chips

In some embodiments, the biosensor device of the present technology comprises a detection chip. In some embodiments, the detection chip has similar structural and functional characteristics as those disclosed in the '898 patent. For example, the detection chip can include a wafer or substrate made from silicon oxide. The substrate can be coated with a graphene surface. Electrodes are provided on the graphene layer, and a solution reservoir is created by an insulating the electrodes with, for example without limitation, silicone rubber. In some embodiments, probes (e.g., aptamers) are brought into contact with the graphene layer for detection of particular targets of interest.

In some embodiments, a current to voltage (I-V) curve of the detection chip can be generated in the absence or presence of target molecules. Without being held to any particular theory, attachment of probes (e.g., aptamers) to the graphene layer increases the resistance of the graphene layer, which results in a baseline I-V curve for the detection chip in the absence of any target molecules. Hybridization of the probe with the target molecule may generate a change in the affinity between the probe and the graphene layer, thereby resulting in changes in the resistance of the graphene layer, detectable by a shift of the I-V curve compared to the baseline curve. The more the probes hybridize or if more target molecules hybridize, the larger the change in resistance, and the greater the shift in the I-V curve, which provides a way to determine not only the presence of the targeted molecule but also a detected concentration of the target molecule.

Examples of Aptamer Probes

In some embodiments, the detection chip of the biosensor device comprises a probe specific for a target molecule associated with a pathogen of interest for detection of the presence of the pathogen. In some embodiments, the probe comprises an aptamer for specific recognition of target molecules, for example, DNAs, RNAs, or proteins associated with a pathogen of interest, for example, a virus (e.g., the SARS-COV-2 coronavirus). Aptamers are often oligonucleotide or peptide molecules that are designed and generated to specifically bind to targets of interest, such as proteins or nucleic acids. Aptamers can be made from nucleic acids (RNA or DNA) or peptides. In some embodiments, the aptamer comprises nucleic acid and is single-stranded. In other embodiments, the aptamer comprises nucleic acid and is double-stranded.

In some embodiments, the detection chip may be configured with a particular aptamer to detect the presence of a specific target DNA, RNA, or protein, and the aptamer may be either natively (e.g., manually) or synthetically (e.g., using an automated high-throughput deposition system) attached to the detection chip. In some embodiments, the detection chip can include multiple aptamers each targeting a particular DNA, RNA, or protein of interest. In some embodiments, the multiple aptamers can be arranged in an array for testing the presence of one or a plurality of target DNAs, RNAs, or proteins associated with one or multiple pathogens of interest.

In some embodiments, the aptamer-based detection chip can detect the presence of a target molecule (e.g., protein, nucleic acid, virus) by a change in the light refracted, reflected, fluoresced, absorbed and/or emitted by the detection chip. Alternatively, the aptamer-based detection chip can utilize changes in impedance, resistance, capacitance, voltage, current, resistance, any combination thereof, or changes in the electric field to indicate the presence of the target molecule bound by the aptamer.

As demonstrated in the working example, the biosensor device of the present technology can be used for rapid and precise detection of a pathogen of interest, for example, the SARS-COV-2 virus. However, the biosensor device can be designed for any other pathogen of interest or constructed to simultaneously detect multiple viruses, for example, common influenza, MERS-COV, SARS-COV, and SARS-COV-2, by modifying the aptamer probes specific for the intended targets. The aptamers can also be adapted for detection of potential future variants of a target pathogen, for example, potential future mutations within SARS-COV-2 genome.

Examples of Biosensor Devices

Figure 2A:
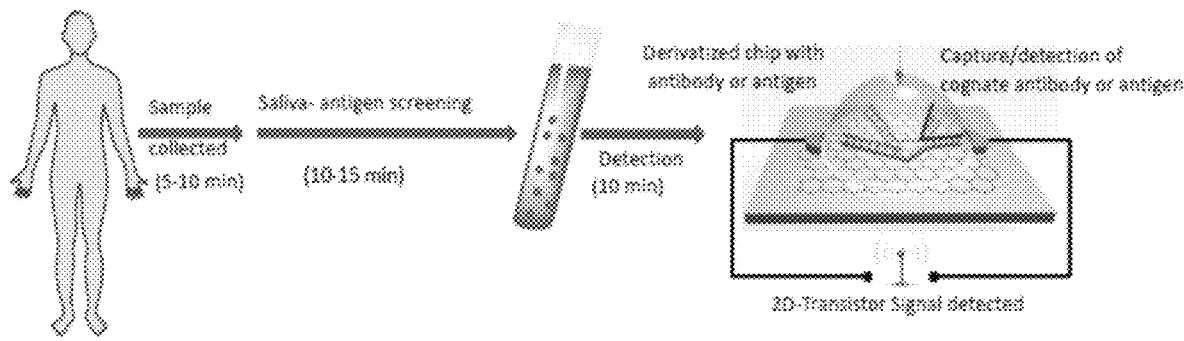
Figure 2B:
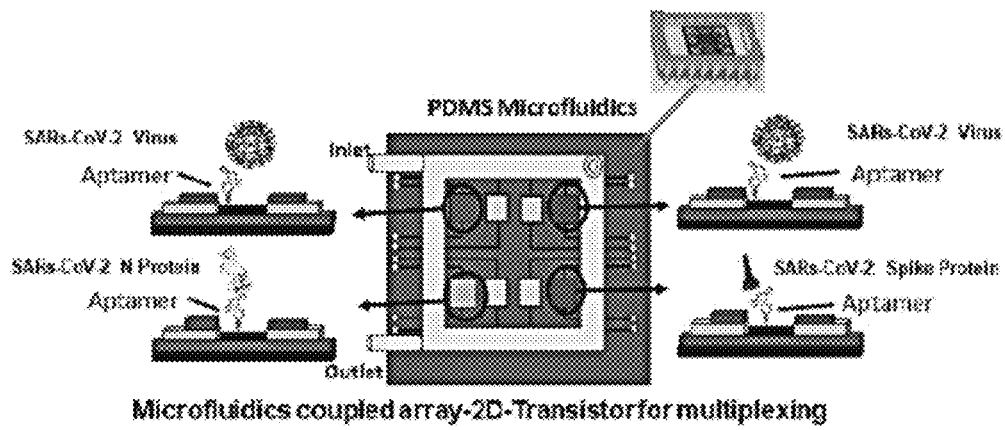
Figure 2C:
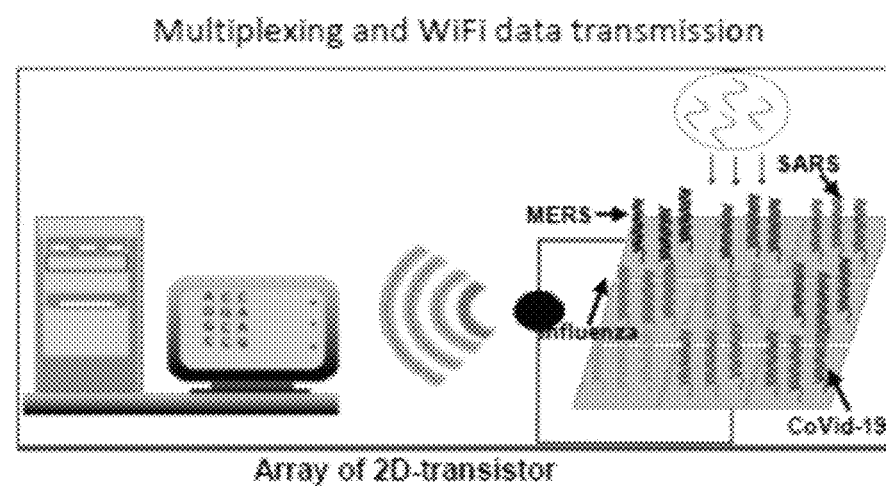
Figure 3:
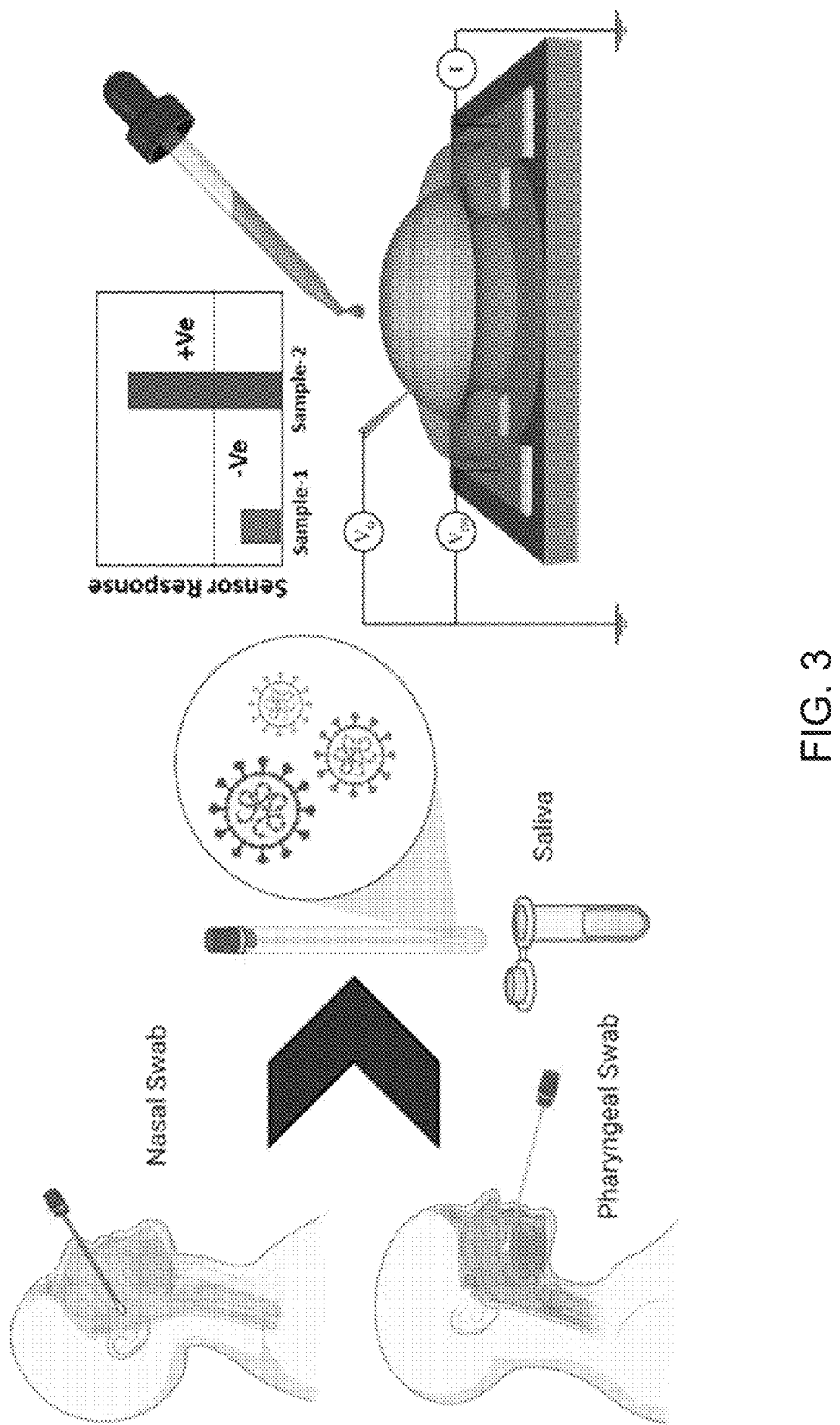
FIG. 3 is a schematic showing the collection of the biological sample and the detection of the pathogen using a handheld device.

In some aspects, a biosensor device is provided for determining the presence of a protein or viral particles in health care-related settings and/or environmental samples (e.g., as shown in FIGS. 1A-1C and 2A-2C), with the collection of the biological sample shown in FIG. 3. In the example shown in FIG. 3, the biological sample containing the protein or viral particle may be collected using a nasal swab, a pharyngeal swab, or saliva. In other examples, exhaled breath or environmental samples (e.g., air, water, household and industrial waste) may be collected. FIG. 3 further shows the sensor response readout, which is validated against cognate proteins and virus samples, may be collected on a handheld device.

In some embodiments, the biosensor device comprises a housing unit having a first opening, a second opening, and a third opening. A cartridge is adapted to be removably fixed within the housing to facilitate the measurements. The cartridge comprises a detection chip that is in electrical communication with a surface of the cartridge during detection of a target. A cap is removably affixed over the second opening, and the cap includes circuitry and a visual indicator. When the cartridge is disposed within the housing with the cap disposed over the second opening, the target-sensing detection chip is disposed in fluid communication with the first opening and the cap is disposed in electrical communication with the surface of the cartridge.

Figure 4A:
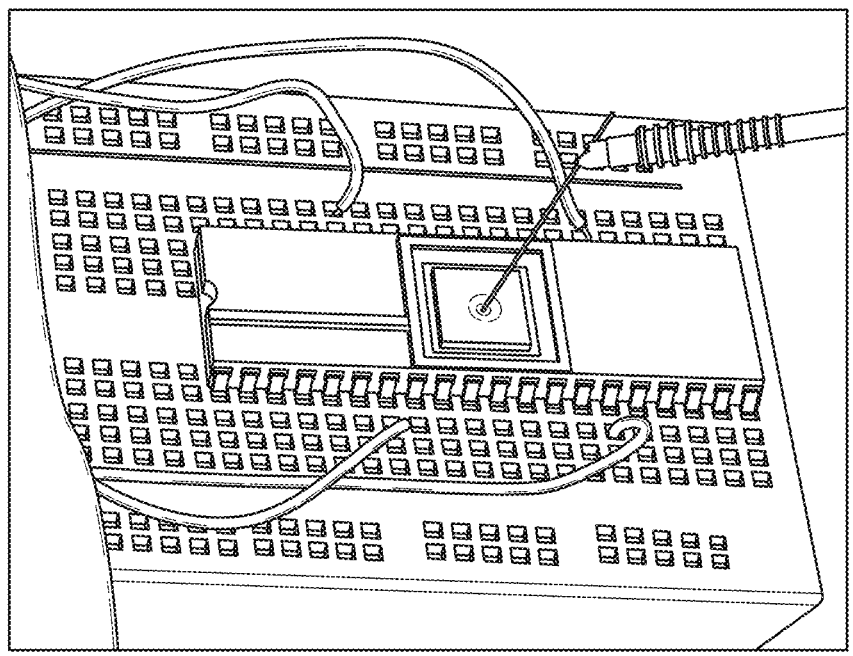
FIG. 4A shows an example of a graphene FET (GFET) sensor on a chip carrier and a breadboard setup for graphene FET sensors.
Figure 4B:
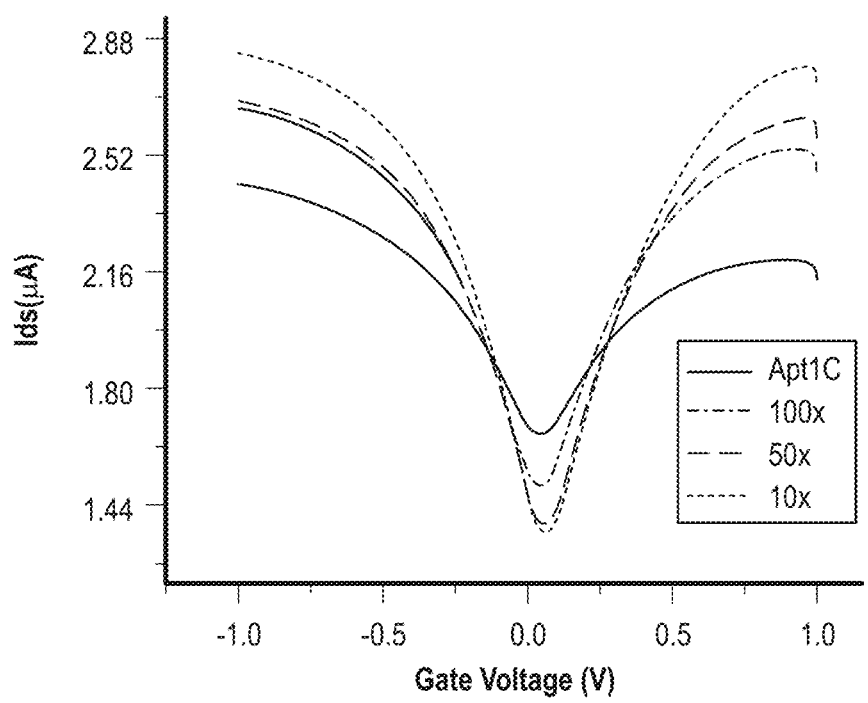
FIG. 4B shows an example drain-source current analysis with respect to gate voltage for the experimental setup shown in FIG. 4A.

In some embodiments, the detection chip (which can be mounted on a breadboard as shown in FIG. 4A) utilizes electron mapping or electron density mapping to distinguish a change in energy between a single nucleotide pair. Such identification of the change in energy determines the proteins that comprise the nucleotide pair. The example setup shown in FIG. 4A results in the drain-source current analysis with respect to gate voltage, as shown in FIG. 4B. In this example, the gate voltage was scanned in the range of +1 V to −1 V with a step size of 2 mV, the drain-source voltage ($V_{ds}$) was 30 mV (which was optimized in the 0-100 mV range in increments of 10 mV), the drain-source current ($I_{ds}$) was on the order of μA, and the Dirac voltage was analyzed at the $I_{ds}$ minima.

In some embodiments, the detection chip, upon detection of one or more targets, for example, viruses, can transmit that information in any of a number of ways. In some embodiments, the detection chip can be connected via circuitry to one or more colored lights, for example LEDs, and signals the illumination of a different color or colors preselected to represent a detection event. The color or colors, or the intensity thereof, or the number of individual LEDs illuminated could also be an indication of the concentration of the detection event. In other embodiments, the detection chip can be electrically connected with circuitry that includes a wireless transmitter that transmits data regarding the detection event to a computer or tablet or other portable or non-portable data storage device for analysis and/or later display.

Figure 5A:
FIGS. 5A-5F show stages in an example fabrication of the graphene FET.
Figure 5B:
Figure 5C:
Figure 5D:
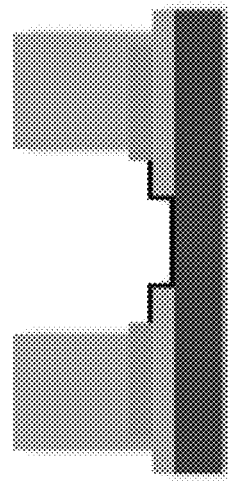
Figure 5E:
Figure 5F:
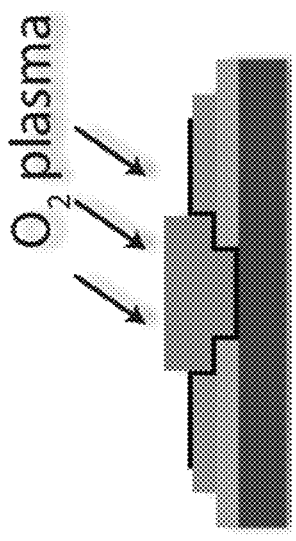

FIGS. 5A-5F illustrate the stages in an example fabrication of the graphene FET. As shown therein, the source drain electrodes (Au/Cr~100 nm) are deposited on an $SiO_2$ substrate (FIG. 5A) using sputtering deposition, which is followed by depositing a passivation layer ($SiO_2$ or $Al_2O_3$~80 nm) on the source drain electrodes (FIG. 5B). In FIG. 5C, the graphene is wet transferred onto the patterned substrate and the Poly(methyl methacrylate) (PMMA) is removed by dissolving with acetone. In the next step, as shown in FIG. 5D, the (polymer, polymethyl glutarimide) (PMGI) photoresist is applied to protect the sensor area, and the extra graphene layer is removed by $O_2$ plasma etching. The PGMI photoresist is lifted off and the graphene FET is annealed in forming gas, e.g., a hydrogen/nitrogen atmosphere (FIG. 5E), and finally polydimethylsiloxane (PDMS) or epoxy is applied to form a well for containing the sample liquid.

In some embodiments, the graphene FET may be configured to detect multiple distinct pathogens by attaching multiple probes (e.g., aptamers) on non-overlapping portions of the graphene FET. Each of the multiple probes attached is selected to bind to different specific proteins. In other embodiments, an array of detection chips can be used to detect multiple distinct pathogens. In this example, each of the multiple probes is attached to a corresponding one of the array of detection chips. Thus, embodiments of the disclosed technology provide alternate ways of detecting multiple pathogens.

Figure 6:
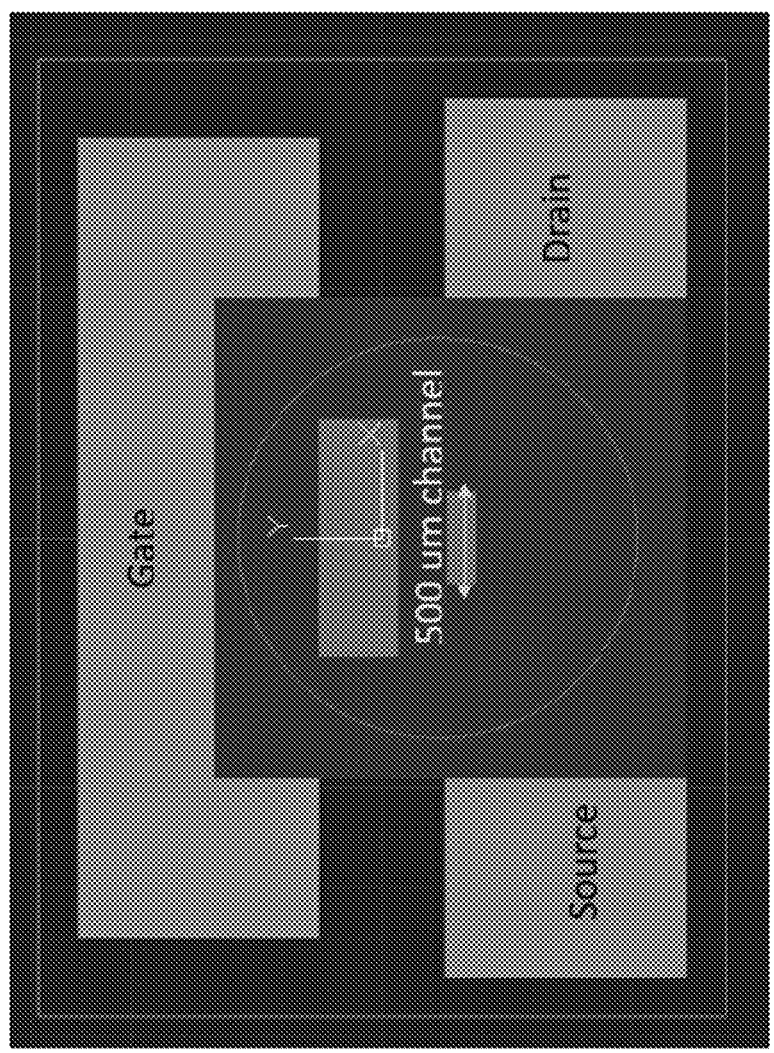
FIG. 6 shows a two-dimensional view of an example graphene FET.
Figure 6:
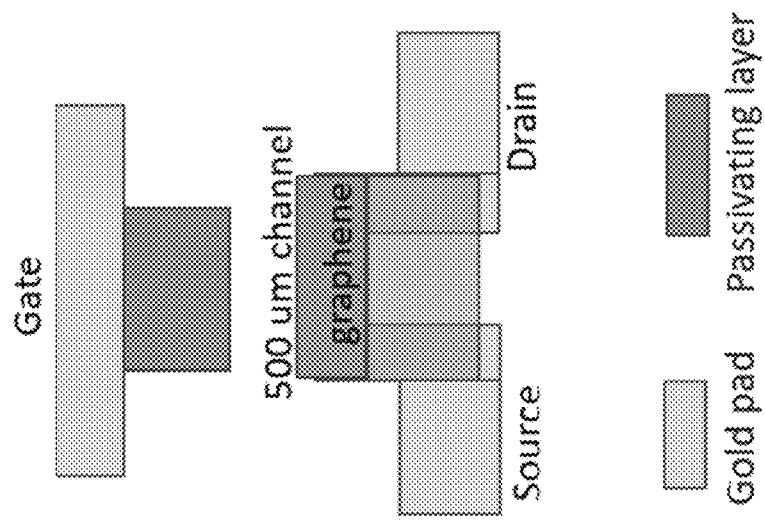

FIG. 6 illustrates a two-dimensional schematic of the graphene FET, wherein the source, drain and gate electrodes are fabricated using gold pads, upon which there are passivating layers, and then the graphene layer. In an example, the graphene FET includes a 500 µm channel in between the passivating layers adjacent to the gate and the drain source electrodes.

Figure 7A:
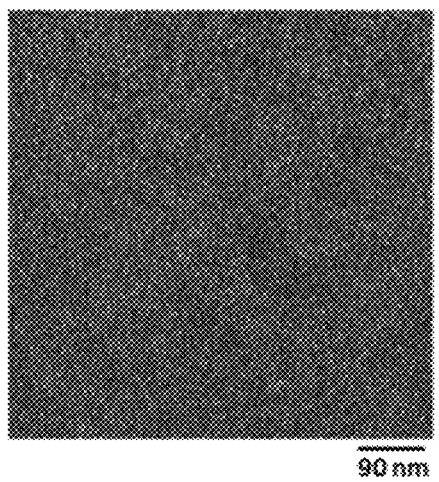
FIGS. 7A-7F show various stages of atomic force microscopic imaging of an example graphene FET.
Figure 7B:
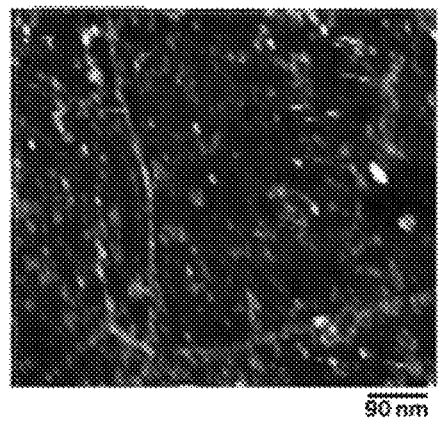

FIGS. 7A-7F illustrate atomic force microscope imaging of the graphene FET after different steps. FIG. 7A shows the bare graphene surface (with a roughness of 0.7±0.3 nm) and FIG. 7B shows the graphene surface after a 5 mM PBASE addition (with a roughness of 1.8±0.5 nm).

Figure 7C:
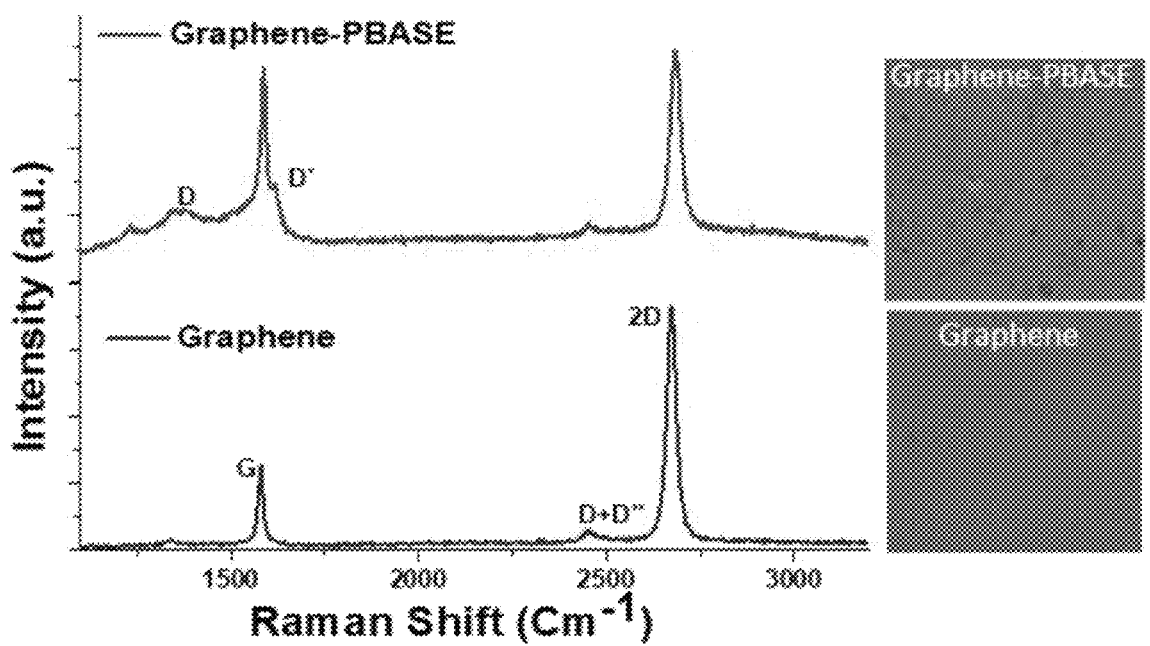

FIG. 7C shows the Raman spectroscopy of pristine graphene and PBASE functionalized graphene FET (with the inset showing the light microscope image of the scanned area). The graphene FET was derivatized using PBASE (5 mM) and was analyzed in variable forward (−1 to +1 V) and reverse (+1 to −1 V) gate voltage swipe of 0.2 V step and variable drain source voltage (Vas) of 0-100 mV with incremental step of 10 mV. In addition to the expected G- and 2D-peaks (with a peak intensity ratio of >1:2, indicating high quality material) on the pristine/untreated sample, the appearance of D and D' peak with the addition of the PBASE might be due to pyrene group binding, and enhanced $sp^3$ bonding.

Figure 7D:
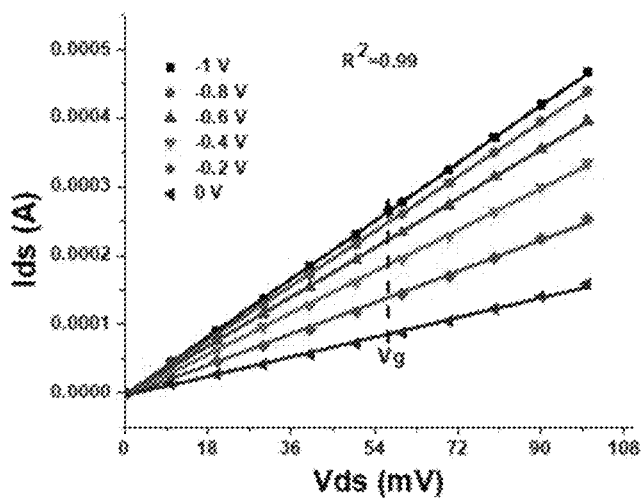
Figure 7E:
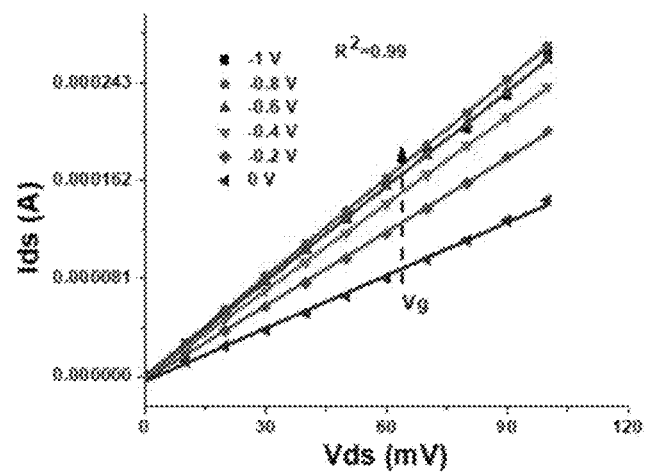
Figure 7F:
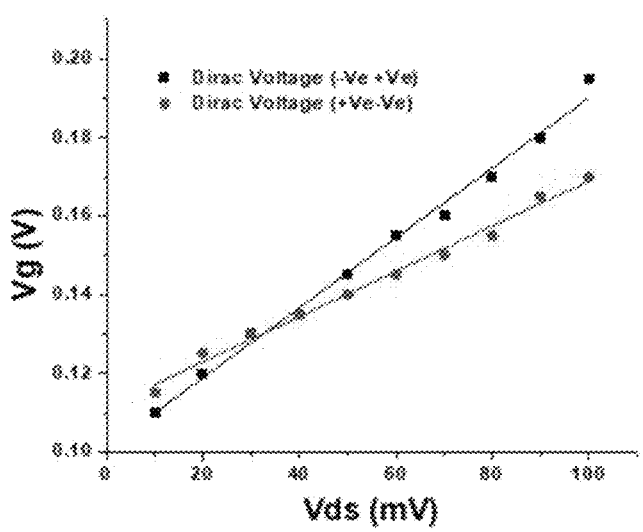

FIGS. 7D and 7E show the drain-source at 0 to −1 V, wherein the $I_{ds}$ of the graphene FET is measured with respect to $V_G$ and $V_{SD}$, respectively. FIG. 7F shows the $V_D$ hysteresis analysis at different Vas when cyclic (back- and forth-) gate voltage sweep in the range of +1 V to −1 V. As evidenced in FIG. 7F, in the range of 20 mV>$V_{SD}$>50 mV there is a minimal hysteresis in the $V_D$.

Figure 8:
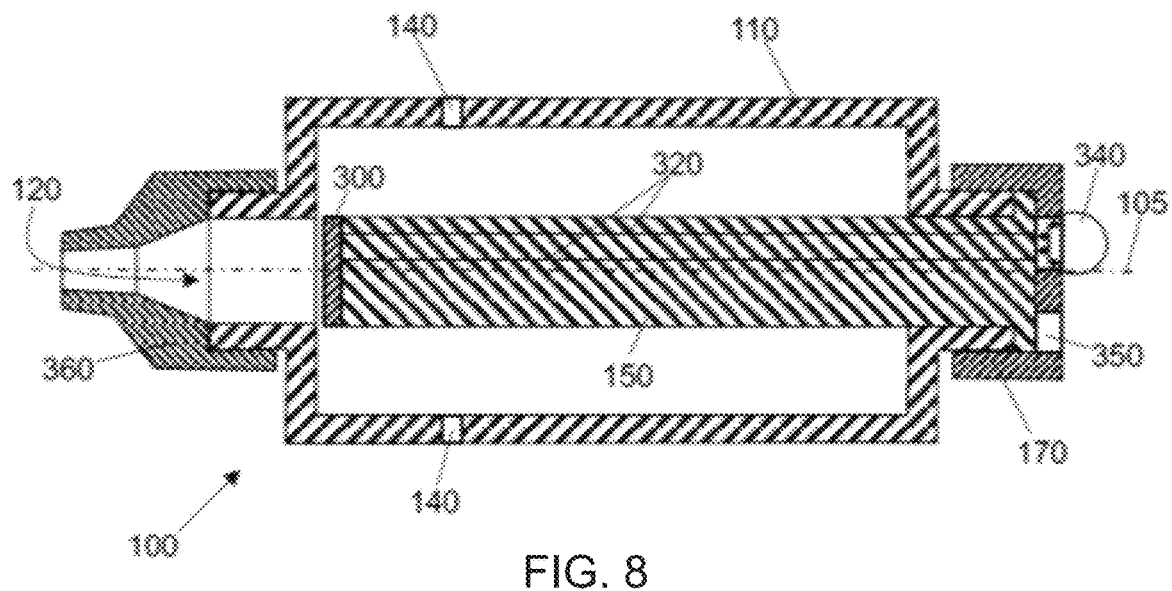
FIGS. 8-11 show partial cross-sectional views of example embodiments of a detection device in an assembled state.
Figure 9:
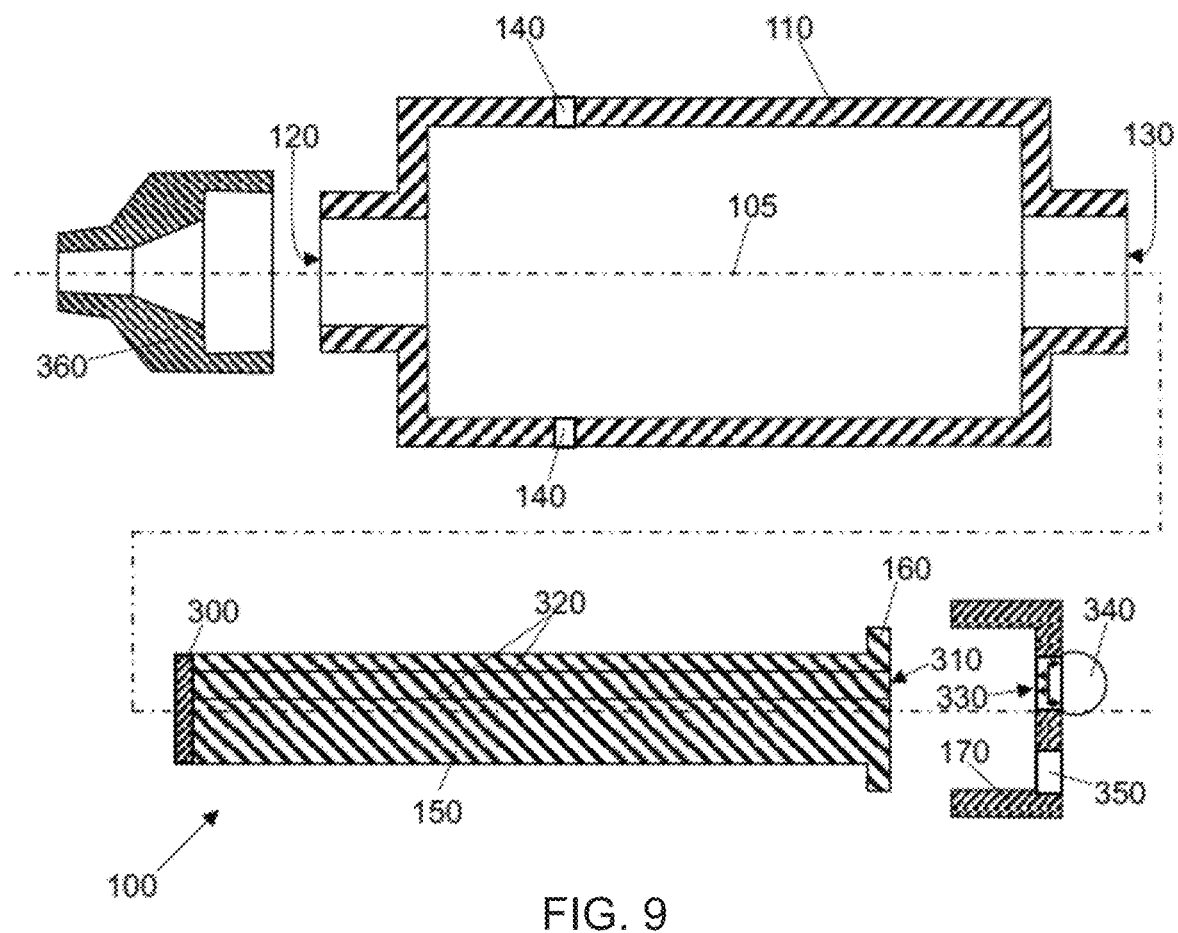

In some embodiments, a schematic representation of a biosensor device 100 according to the present technology is illustrated in partial cross-section in an assembled state in FIG. 8 and shown in partial cross-section with the major components exploded in FIG. 9. As shown therein, the major components include a housing 110 that can, for example, serve as a handle and a chassis for supporting the other major components. In some embodiments, the housing 110 and the major components are arranged along a longitudinal centerline 105. In other embodiments, the components can be arranged in any geometry as aesthetically or functionally may be desirable, for example as illustrated in FIGS. 10 and 11 described further hereinbelow.

Referring to FIGS. 8 and 9, in one embodiment the housing 110 includes a first opening 120, a second opening 130 and at least one third opening 140. An insert or cartridge 150 is adapted to be removably fixed within the housing 110. For example, the cartridge 150 in one embodiment could be removably fixed by a threaded connection through the second opening 130. In another embodiment the cartridge 150 includes a shoulder 160 that extends laterally from an end of the cartridge 150 so that when the cartridge 150 is disposed within the housing 110, the shoulder 160 overhangs an edge of the second opening 130 and is compressively held against the edge of the second opening 130 by a cap 170 that attaches, for example by threads, over the shoulder 160 of the cartridge 150 at the second opening 130. In other embodiments the cartridge 150 could be removably fixed within the housing 110 by either of the above disclosed mechanisms and/or by a press fit or a magnetic attachment or any single attachment mechanism or combination of attachment mechanisms as known in the art.

Figure 10:
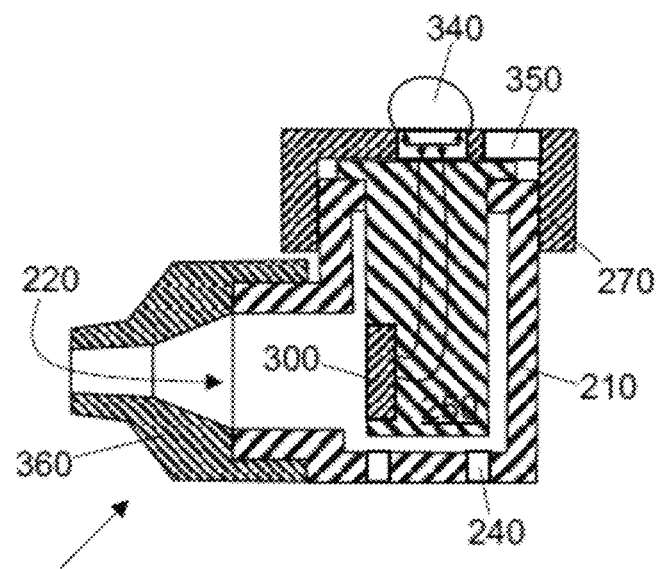
Figure 11:
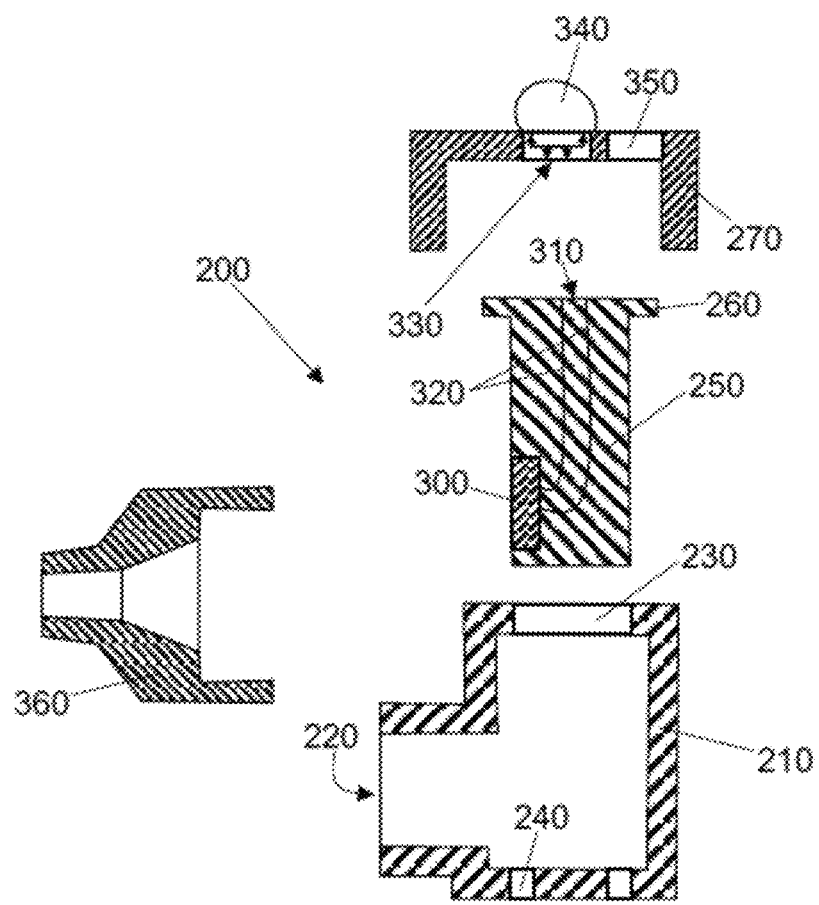

Referring to FIGS. 10 and 11, in another embodiment of a device 200, a housing 210 includes a first opening 220, a second opening 230 and at least one third opening 240. In this embodiment an insert or cartridge 250 is adapted to be removably fixed within the housing 250. For example, the cartridge 250 in one embodiment could be removably fixed by a threaded connection through the second opening 230. In another embodiment the cartridge 250 includes a shoulder 260 that extends laterally from an end of the cartridge 250 so that when the cartridge 250 is disposed within the housing 210, the shoulder 260 overhangs an edge of the second opening 230 and is compressively held against the edge of the second opening 230 by a cap 270 that attaches, for example by threads, over the shoulder 260 of the cartridge 250 at the second opening 230. In other embodiments the cartridge 250 could be removably fixed within the housing 210 by either of the above disclosed mechanisms and/or by a press fit or a magnetic attachment or any single attachment mechanism or combination thereof as known in the art.

Regardless of the geometry of the housing 110, 210 in regard to how the major components fit together, whether as shown in FIGS. 8-11 or using other geometries as are known in the art for a housing with an insertable and removable insert or cartridge, all embodiments of the cartridge 150, 250 include a detection chip 300 that is in electrical communication with a surface 310 of the cartridge 150, 250.

In some embodiments the detection chip 300 is reusable through a cleansing process so that the cartridge 150, 250 on which it is disposed is also reusable. In other embodiments the detection chip 300 is a single use chip so that the cartridge 150, 250 is a disposable cartridge 150, 250. The detection chip 300 is electrically communicative to the surface 310 for example, wirelessly, via wires 320, or traces or an internal circuit board having wires or traces.

Still referring to FIGS. 8-11, in some embodiments a cap 170, 270 attaches, for example by threads, over the second opening 130, 230 so that circuitry 330 within the cap 170, 270 is in electrical communication with the surface 310, and therefore also in electrical communication with the detection chip 300. The cap 170, 270 in other embodiments attaches over the second opening 130, 230 by a press fit, a snap fit, a magnetic attachment, a latch mechanism or by any other mechanism for removable attachment as may be known in the art.

The circuitry 330 is of the type as known in the art that can interface with a signal from the detection chip 300 and relay or send an independent signal to a visual indicator 340 disposed on an outside of the cap 170, 270. The visual indicator 340 in one embodiment is one or more LEDs but in other embodiments can be one or more incandescent bulbs, an LED or LCD digital display, or other sorts of visual indicators as may be known in the art. Like the description hereinabove for the detection chip 30, the visual indicator 340 signals the illumination of a different color or colors preselected to represent a detection event. The color or colors, or the intensity thereof, or the number of individual LEDs illuminated could also be an indication of the concentration of the detection event. In another embodiment the visual indicator 340 is electrically connected with the circuitry 330 that includes a wireless transmitter that transmits data regarding the detection event to a computer or tablet or other portable or non-portable data storage device for analysis and/or later display. As illustrated in Figures FIGS. 8 and 10, when the cartridge 150, 250 is removably fixed within the housing 110, 210 with the cap 170, 270 disposed over the second opening 130, 230, the detection chip 300 is disposed in fluid communication with the first opening 120, 220.

Figure 12:
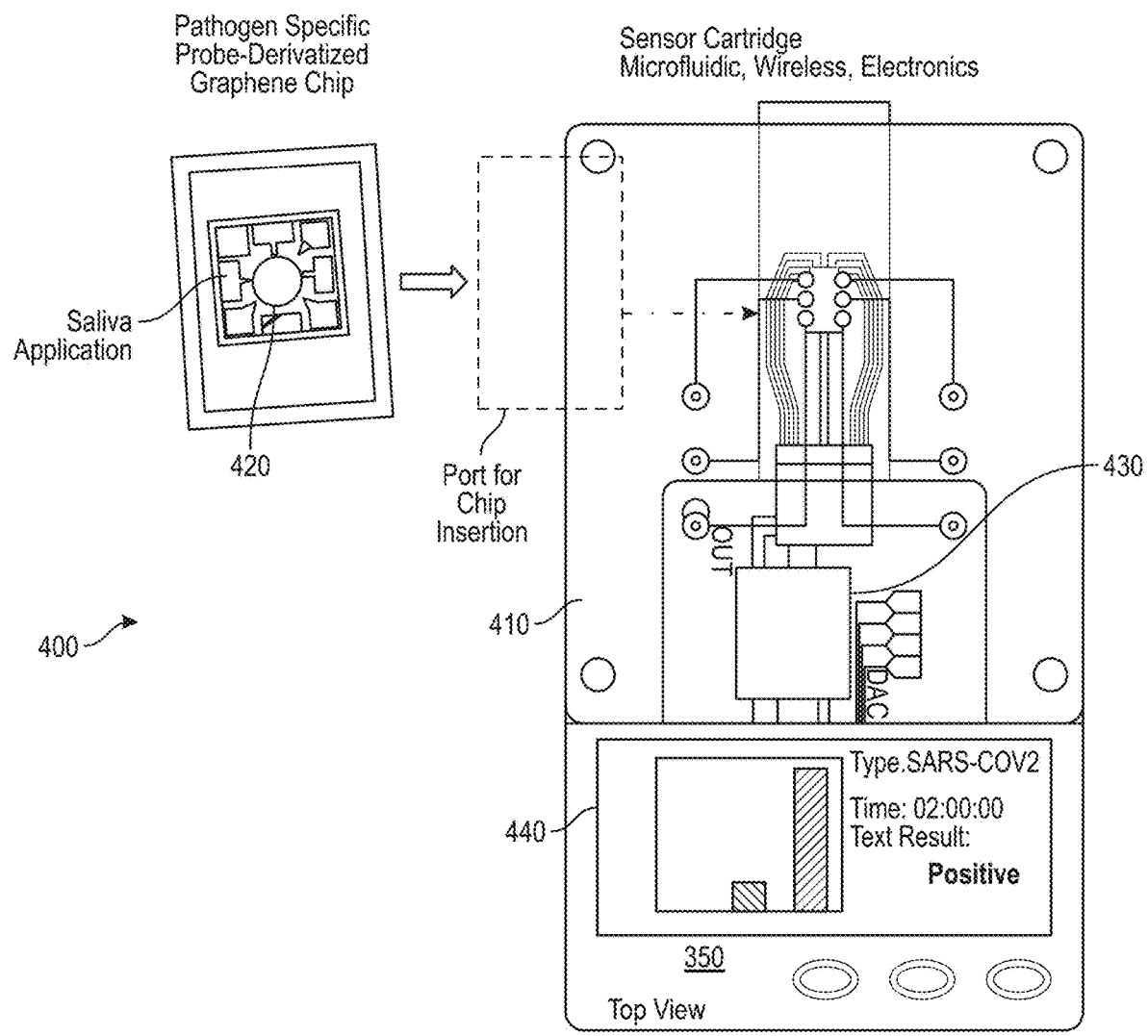
FIG. 12 shows another example embodiment of a detection device.

Referring now to FIG. 12, in another embodiment of a device 400, a housing 410 includes a port for insertion of a detection chip 420 having all the structural and functional features of the detection chips. In this embodiment the housing 410 further includes circuitry 430, and a visual indicator 440, both of which function the same as the circuitry 330 and visual indicator 340 described hereinabove. The detection chip 420 when inserted into the housing 410 functions in the same way as the detection chip 300 by having electrical connections on a side that communicate electrically with the circuitry 430. In this embodiment, the detection chip 420 can be exposed to sample molecules, for example, by applying saliva to the chip 420 or by breathing or coughing onto the chip 420.

Referring to any of the embodiments in FIGS. 8-12, a power source 350, for example one or more batteries or a battery pack is schematically shown as disposed within the device 100, 200, 400 and is in electrical communication with the circuitry of that embodiment. For example, in the embodiments shown in FIGS. 8-11 the power source 350 is disposed within the cap 170, 270 and is in electrical communication with the circuitry 330. Therefore, when the cap 170, 270 is installed on the housing 110, 210, the power source 350 is also in electrical communication with the surface 310, and therefore is further in electrical communication with the detection chip 300. Therefore, the power source 350 can provide electrical power not only to the internal circuitry 330 within the cap 170, 270, but can also provide electrical power to the detection chip 300 when the device 100, 200 is assembled.

Still referring to FIGS. 8-11, in some embodiments a disposable mouthpiece 360 is removably attachable over the first opening 120, 220. In some embodiments the disposable mouthpiece 360 attaches, for example by threads, over the first opening 120, 220, whereas in other embodiments the disposable mouthpiece 360 attaches over the first opening 120, 220 by a press fit, a snap fit, a magnetic attachment, a latch mechanism or by any other mechanism for removable attachment as may be known in the art.

In some embodiments prior to operation a fresh unused cartridge 150, 250 is removably inserted into a housing 110, 210 and the cap 170, 270 is affixed to the housing 110, 210. When the device 100, 200 is so assembled, for example, as illustrated in FIGS. 8 and 10, the detection chip 300 on the cartridge 150, 250 is in fluid communication with the first opening 120, 220.

As noted above, a person's breath can carry a virus or tiny aerosolized droplets containing a virus and/or molecular components of said virus and certain viruses can be identified by a target protein or proteins that make up the virus. The detection chip 300, 420 can indicate the presence of the target molecule, protein or proteins associated with the particular virus, for example the SARS-COV-2 virus. Therefore, in operation, a user to be tested for the particular virus breathes into mouthpiece 360 (or otherwise onto the detection chip 300, 420) to test the user for the presence of the SARS-COV-2 virus. If the target molecule, and therefore the particular virus, is detected the detection chip 300, 420 in association with the attached circuitry 330, 430 sends a signal to the visual indicator 340, 440 disposed on the outside of the cap 170, 270 or housing 410. The visual indicator 340, 440 signals the illumination of a different color or colors preselected to represent a detection event. The color or colors, or the intensity thereof, or the number of individual LEDs illuminated could also be an indication of the concentration of the detection event. In another embodiment the visual indicator 340, 440 is electrically connected with the circuitry 330, 430 that includes a wireless transmitter that transmits data regarding the detection event to a computer or tablet or other portable or non-portable data storage device for analysis and/or immediate or delayed detection event display. In some embodiments the visual indicator 340, 440 can additionally flash and/or illuminate to signal a malfunction, low battery, or other error or problem.

Returning now to FIGS. 8-11, third openings 140, 240 allow for the user's breath to exit the housing 110, 210 without causing a pressure buildup therein. Making the mouthpiece 360 disposable allows for a fresh mouthpiece 360 to be installed on the device 100, 200 prior to each use thus lowering the risk of contamination between those persons tested.

In other embodiments illustrated for example as portions of FIGS. 8 and 10, the cartridge 150, 250 and cap 170, 270 can be attached to one another directly by any of the method of attachment as described hereinabove or as otherwise known in the art and without the housing 110, 210. In these embodiments a user need only breathe onto the detection chip 300 to be tested for the presence of a target protein and therefore the associated virus.

In any of these embodiments, the biosensor device can be embedded in different assemblies and products, or appended, affixed, or removably affixed to clothing or hats via a clip, hook and loop fastener, or other fastening mechanisms known in the art that can accommodate a detection chip of this invention and hook or append the same to a target surface, such as, for instance, a hat or a mask. Moreover, the detection chip can be replaceable or disposable. Furthermore, the detection chip can be used to detect more than one virus' presence by including an aptamer specifically created to detect the presence of each of a plurality of different virus' nucleic acid or protein with particularity, each being identifiable by having a different color or colors, or illumination pattern coordinated with a detection event.

There are several unique features of the provided biosensor device. For example, first, the biosensor device possesses multi-target diagnostic capabilities, including (i) detection of viral particles with a resolution of less than 7 particles/sample; (ii) detection of molecular components of said virus, including viral proteins, with detection limit in low nanomolar range; and (iii) detection of nucleic acids with single nucleotide resolution and femtomolar sensitivity. Second, the sensor surface is specifically processed and tuned to be charge sensitive to a higher degree of specificity.

Third, electrical recording and electronic data analysis algorithm are designed to increase S/N ratio to distinguish smallest change in the Dirac potential minima. This allows for recording interaction of sample (e.g., virus, spike proteins) to probe (e.g., aptamer) at the highest resolution (lowest number) with low power consumption. These features allow miniaturization and portability of the device.

Because of the design features, the biosensor device can achieve the following: (i) read-out in 10 minutes; (ii) sample can be from saliva, aerosols, and body fluids, e.g., nasal or nasopharyngeal; (iii) high accuracy (~95%); (iv) sensitivity to as few as 20-30 viruses which enables early detection; (v) wireless contact tracing; (vi) portability with low power (9V battery) requirement and cell phone-comparable dimension; (vii) inexpensive mass production ($10/test) capability; and (viii) non-technical operation requirement, i.e., easy-to-use with layman's training without any medical professional help.

Examples of Using the Biosensor Device for Rapid Covid-19 Testing

Figure 13A:
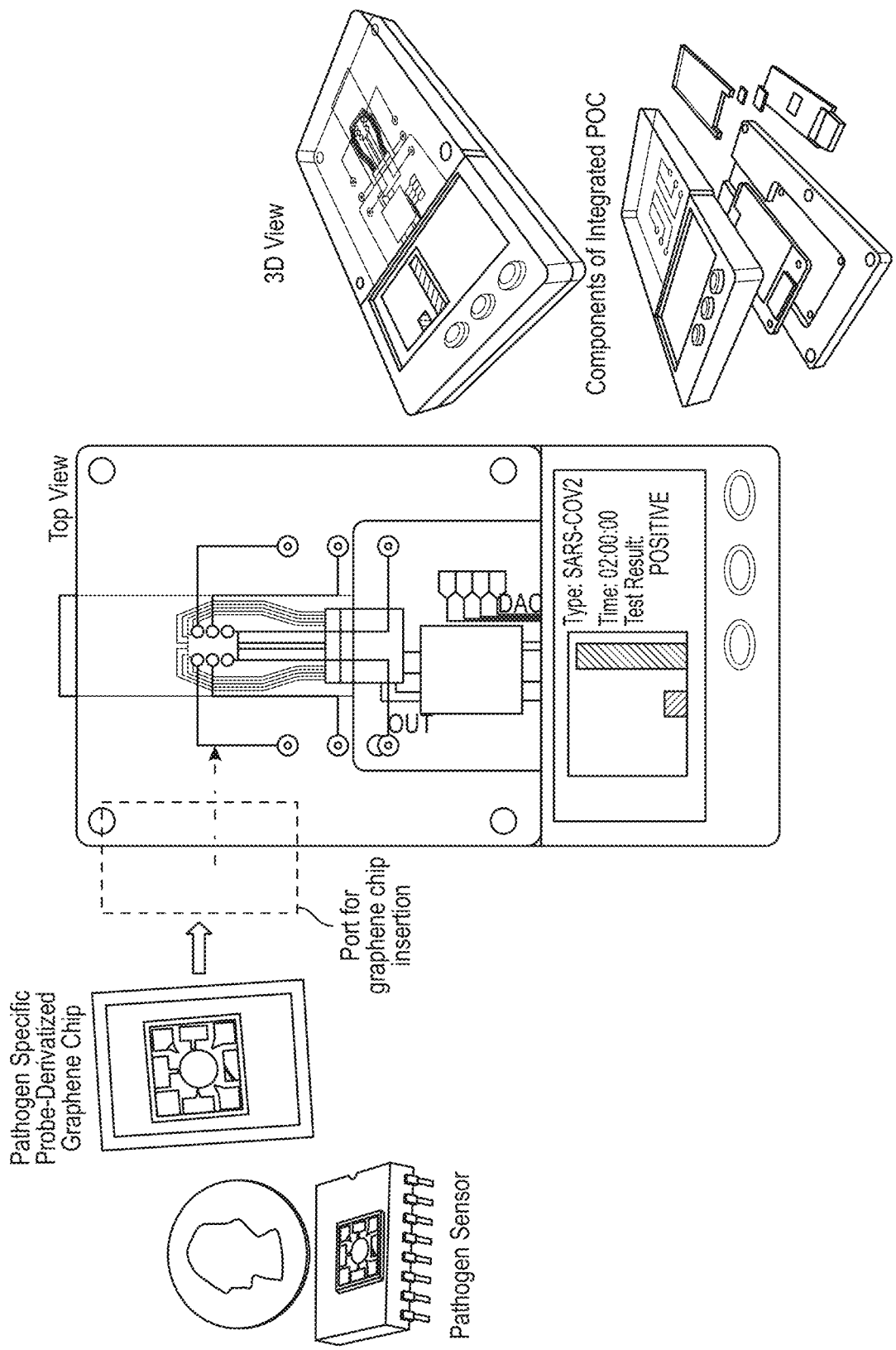
FIGS. 13A and 13B show examples of assembled portable, compact devices.
Figure 13B:
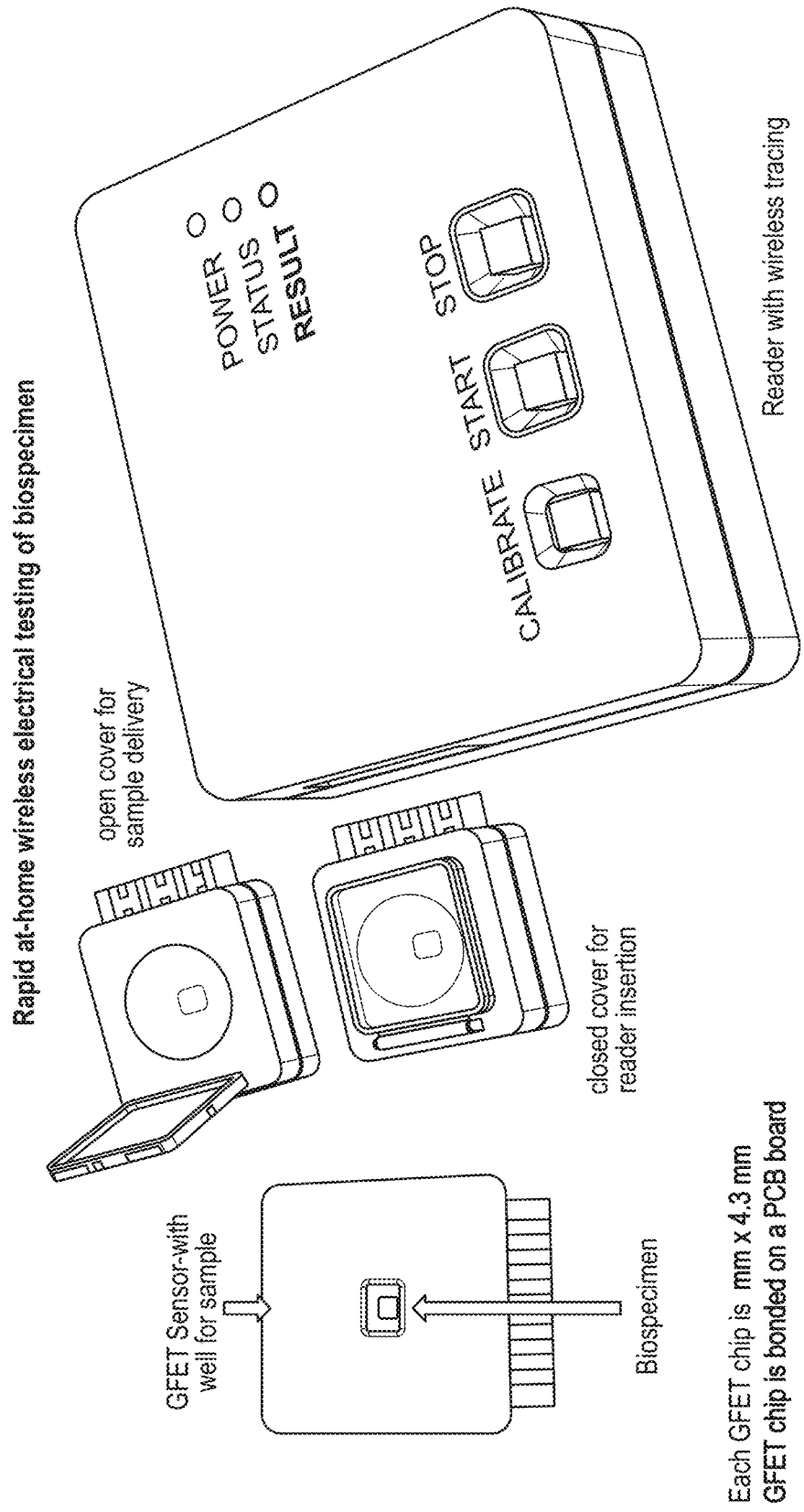
Figure 14:
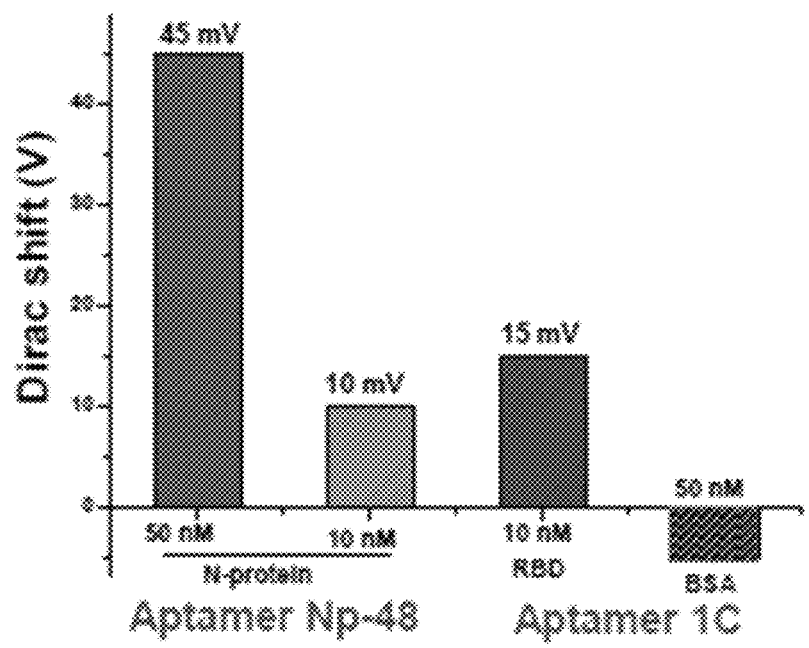
Figure 15:
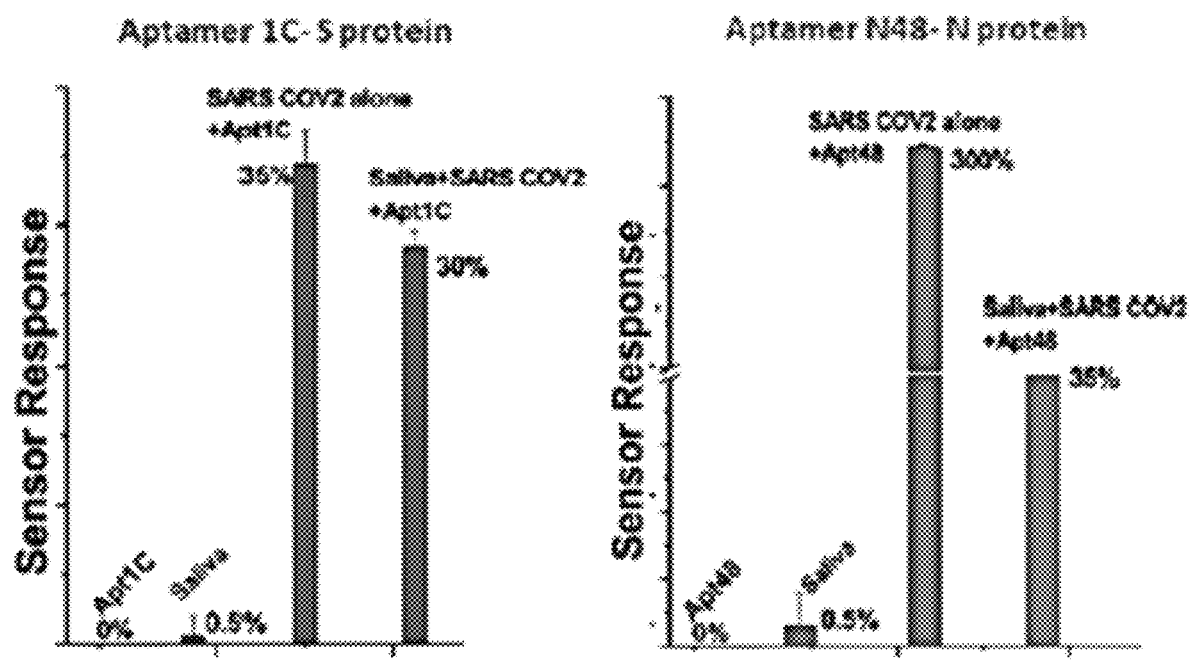

In this example, a portable diagnostic device for highly specific and sensitive detection of coronavirus SARS-COV-2 was developed (FIGS. 1A-1C and 2A-2C). The device contains high affinity aptamers against the spike proteins of SARS-COV-2 for active virus screening and records an electrical output to indicates a positive response. The device has in-built wireless functionality which allows rapid tracing and communication with interested decision makers (e.g., doctors, administrators, policy makers). The final assembled portable and compact device, with electronics integrated with the sensor chip, is shown in FIGS. 13A and 13B. It includes a readily integrable genomic information workflow, using a microfluidic module to achieve genome-scale coverage with limited pre-processing and will allow diagnosing potential future mutations within SARS-COV-2 genome, using aptamers against such variants. A patient sample can be tested using the multi array-sensors and the positive/negative results will be transmitted wirelessly.

Although originally developed for RNA/DNA detection at a 10 XM sensitivity, the device has been adopted to derivatize DNA aptamers to the 2D-transistor to recognize their cognate partner within the microfluidic device (FIG. 2A, right). Electrical signals resulting from the interaction of the sample with their specific bait and prey are recorded digitally and transmitted by the integrated wireless system (FIG. 2C). As designed, the device enables concentration and specificity determinations of antibodies, and detection and concentrations of antigens.

Figures 16, 17:
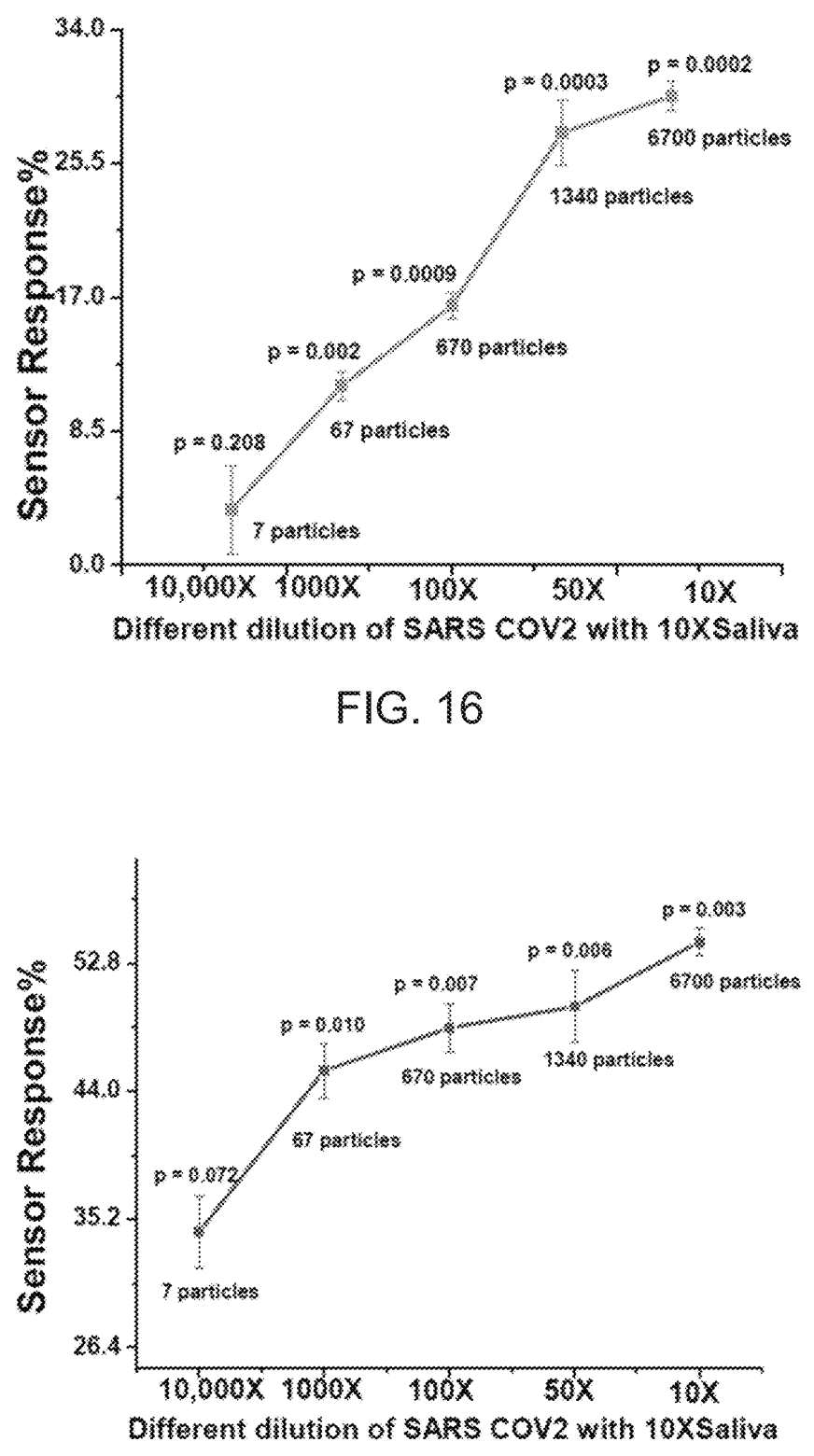

In this example, the device focused on the receptor binding domain of SARS-CoV-2 and specific fragments of the Spike protein, and DNA aptamer sequences specific for these antigens were used. An electrical output response indicates a positive response. As shown, the electrical graphene FET (GFET) sensor can detect as low as 7 viral particles from diluted human saliva samples, without qPCR amplification, in 10 minutes using aptamers specific to two different viral proteins: Aptamer Np-48 (Aptamer 48) specific to the N-protein and Aptamer 1C specific to the S-protein (FIGS. 14-17), suggesting high specificity and sensitivity for SARS-COV-2 testing. In particular, FIGS. 16 and 17 illustrate sensor response plotted on the y-axis against varying degrees of dilution of SARS-COV-2 virus-containing saliva samples plotted on the x-axis for Aptamer Np-48 and Aptamer 1C, respectively. Individual data points are labeled to indicate the number of the virus particles detected. The detection chip has demonstrated the ability to detect as few as 7 virus particles.

Embodiments of the disclosed technology use aptamer derivatized GFETs for label free detection and reporting of SARS-COV-2 and its variant (N501Y, D614G, and Y453F) antigen, which enables the detection of SARS-COV-2 antigen, aptamer for S-protein (Aptamer 1C Kd≈5.8 nM)[4] and N-protein (Aptamer Np-48 0.5 nM)[5] based on their affinity. Both the aptamers were modified for GFET derivatization at 3' end to functionalize the graphene surface. Further, both aptamers were analyzed for the S-protein receptor binding domain (RBD) and N-protein using cognate proteins, inactive virus, and retrospectively RT-PCR validated oral samples.

Materials. The results presented herein were obtained by designing HPLC grade 3' amino functionalized aptamers for N-protein (Aptamer-N)[5] and spike RBD (Aptamer-S)[4] to integrate with GFET. Molecular biology grade 1λPBS (Gibco), $MgCl_2$, and Ultrapure water (Invitrogen) were used throughout the study. Analytical grade 1-pyrenebutyric acid N-hydroxyscuccinimide ester (PBASE) and ethanolamine were used without further processing.

Aptamer derivatization on GFET. The selected aptamers were amino derivatized at 3' end using linker molecule and labeled as Aptamer-S for spike RBD protein[4] and Aptamer-N[5] for Nucleocapsid protein. The aptamers were dissolved in 1×PBS buffer containing 0.5 mM $MgCl_2$ and annealing was performed by control heating at 94 C for 2 min and slow cooling to room temperature. The annealed aptamer was stored at −20 C for further usage. Derivatization was performed by adding 1 μM of aptamer on PBASE functionalized GFET for 30 min. Excess of aptamer was washed and unreacted PBASE were passivated using 10 mM ethanolamine (EA) solution for 20 min. The excess EA was washed and GFET measurement performed in 1×PBS buffer.

Nucleocapsid and spike RBD domain detection. Baseline correction was performed using Aptamer functionalized GFET by sweeping the $V_G$ within the range of ±0.5 V while drain-source voltage maintained at fixed voltage (100 mV). The concentration dependent sensor response was analyzed at different concentrations of cognate proteins (RBD (10, 20, 50, 100, 200 nM))[4] and (Nucleocapsid ~0.5, 1, 5, 10, 20, 50, 100 nM)[5]. After 10 min incubation, excess protein was washed three times using 1×PBS buffer and transfer function ($\Delta V_D$) for sensor was analyzed. The sensor response was calibrated through a $V_D$ shift per the following relation:

$$\Delta V_D = V_D - V_D^0.$$

Herein, $V_D$ is the $V_D$ after addition of sample on chip, $V_D^0$ is the $V_D$ with aptamer derivatized chip, and the percentage response is calculated with respect to $V_D^0$ (i.e., $(\Delta V_D/V_D^0) \times 100$). Furthermore, the aptamer-GFET sensor to detect SARS-COV-2 variants of concern such as B.1.1.7 (N501Y), Y453F and D614G[6-8] using different concentration of recombinant RBD proteins. Two different concentration (100 fM, 100 nM) of mutant variant were utilized and the response compared with that obtained for the RBD of SARS-COV-2.

Inactive virus detection in simulated conditions. The related experiments were performed by preparing diluted solutions containing heat inactivated SARS-COV-2 (USA-WA1/2020**, 9.55×10⁶ $TCID_{50}$/ml, Zeptometrix). The PFU/mL was calculated as described by Ding et al[9]. The effect of the increment of virus dilution (6.68-6.68×10^6 PFU/mL) on GFET sensor response was measured. 10 µl sample was added on the chip and incubated for 10 min and the $V_D$ shift was measured in the $I_{ds}$-$V_G$ characteristics.

Specificity analysis. To analyze the specificity of the GFET sensor two different concentrations of cognate proteins for MERS-COV, SARS-COV, SARS-COV-2 were analyzed. Sensor response at an ultra-low concentration (100 fM) as well as in the saturation ranges (100 nM) using aptamers for RBD and N protein were investigated.

To analyze the sensitivity and specificity of different concentration of cognate N and RBD proteins (100 fM-100 nM) of MERS-COV, SARS-COV, SARS-COV-2 were used. Concentration dependent analysis was performed by using different dilutions of inactive MERS-COV and SARS-COV-2 viruses (670 PFU/mL-6.7×10^5 PFU/mL) in the simulated conditions described above.

Clinical sample analysis. The oral samples of patients were collected by trained clinician in 3 ml of (0.9% w/v) saline approved by CDC and further tested by CLIA certified lab by trained clinician. RT-PCR analysis was performed using FDA approved Promega RT-PCR test kit for SARS-COV-2 while 10 µL of aliquot of same sample was used in the CLIA lab using GFET sensor and handheld reader. The Aptamer-S showed higher sensor response with inactive virus in simulated environment and was used for all the patient sample diagnosis. A total of thirty patient samples were tested and compared retroactively with RT-qPCR (Ct value≤35) data. The known RT-qPCR negative data was used to set the sensor response threshold value with 99.7% of confidence interval (CI) using ±3σ analysis to predict negative patient samples. The sensor response value above the Mean+3σ was assigned as positive. The positive percent agreement (PPA) and negative percent agreement (NPA) of test were calculated as described FDA guidelines[10].

The limit of detection (LoD) and limit of quantification (LoQ) of sensor were estimated using standard deviation of the response and the slope method[10]. All the data presented were the mean of at least three measurements and error of one standard deviation (SD).

Figure 18A:
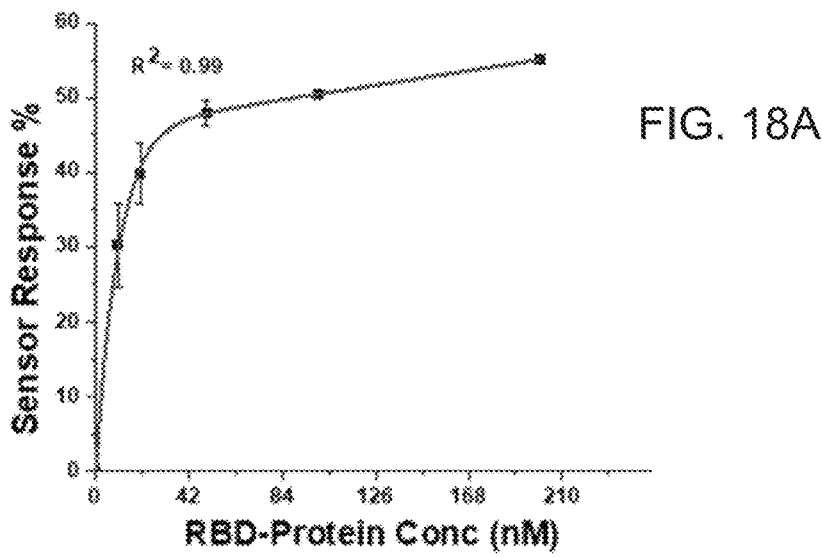
FIGS. 18A-18C shows an example Aptamer-S and Aptamer-N derivatized GFET sensor response due to binding of different concentration of RBD region and N-protein of SARS-COV-2.
Figure 18B:
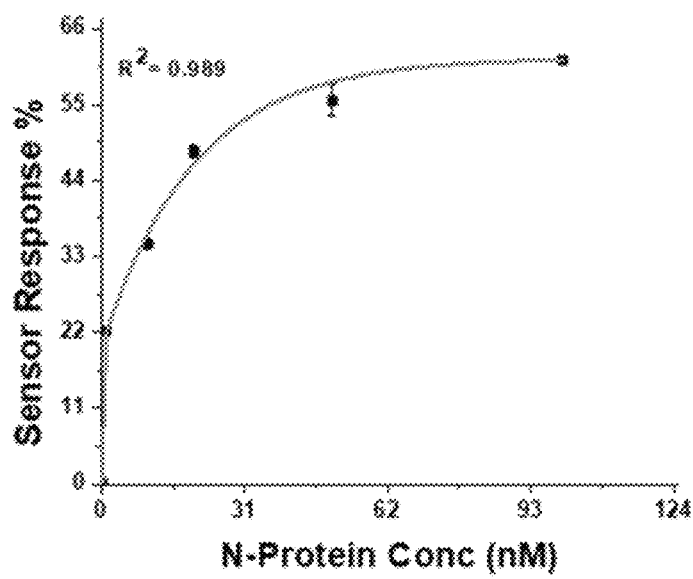
Figure 18C:
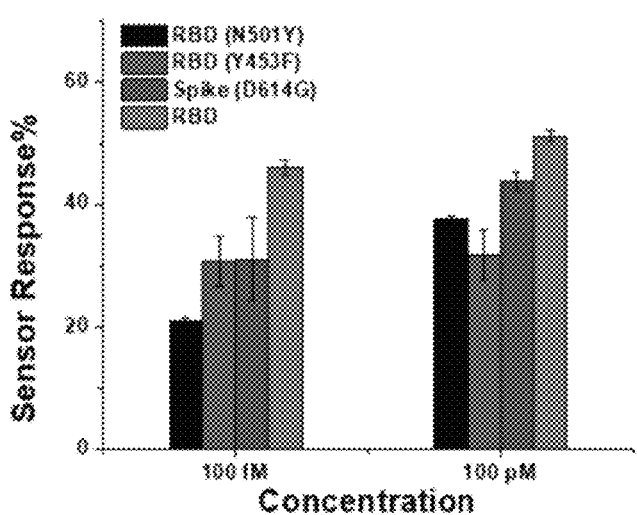

Analysis of the SARS-COV-2 and its mutant antigen. Due to wide range of viral load in a patient sample (10^4-10^7 copy number/mL and 3.48 fM-58.9 nM of antigen level)[11][12], the concentration dependent sensitive region as well as the saturation of sensor response were analyzed. The analysis of Aptamer-S and -N GFET sensor response in different concentrations of RBD and N protein of SARS-COV-2 indicated a concentration dependent exponential shift in the $V_D$, as shown in FIGS. 18A-18C. As shown therein, the sensor reached saturation at 200 nM of RBD (FIG. 18A) and 100 nM of N-protein (FIG. 18B). It was observed that all of the tested concentration of antigen ≥20% sensor response and after saturation, the excess antigen level did not reduce the sensor response below 20% of response. This suggests that the GFET sensor reduces the chances of missing the positive signal due to hook effect as in the case of flow-based antigen testing[13][14].

The antigen test approved by FDA under emergency use authorization (EUA) (shown below in Table 1) did not indicate the ability to detect new variant/s which may escape immunity generated by available vaccine or past infection[15]. There has also been considerable concern[16] about false negatives of the recommended tests. The evolution of new mutations of SARS-COV-2 (B.1.1.7 variant (N501Y), mink-related mutation (Y453F), mutation at S2 domain (D614G) are major matters of concern[17]. Considering the importance of such issues, the GFET sensor was deployed on different SARS-COV-2 mutants. It was indicated, through such tests, that Aptamer-S showed more than 20% of sensor response with 100 fM-100 nM concentration of respective proteins (as shown in FIG. 18C). Although, there is variant specific variability in sensor response observed; however, sensor response was always above the threshold value for positive sample (e.g., >20%) (see FIG. 18C). Based on the concentration dependent analysis of cognate RBD and N protein on respective aptamer derivatized GFET sensors with the SARS-COV-2 variant, embodiments of the disclosed technology can detect relevant viral antigen at fM-nM concentration levels. A reason for the enhanced sensitivity, as well as the concomitant specificity, is due to non-overlapping binding site of aptamer-S at spike protein amino acid T500, N437, and Q506[4] with new mutations.

TABLE 1

Comparison of point of care (POC) antigen test data collected from the FDA Emergency Use Authorization (EUA)

| Entity | Target/Readout | LOD | NPA % (n)/ PPA % (n) | Time (min) |
|---|---|---|---|---|
| PIVOT-Apta-Sensor (current) | S/N proteins, S Mutant proteins, Droplet, Current-Voltage, | Aptamer-S 1.28 PFU/mL and aptamer-N 1.45 PFU/mL | 100 (16)/ 100 (14) | 15< |
| BinaxNow Ag Card | N protein, N.A., LF, | 140.6 TCID$_{50}$/ml | 98 (111)/ 83.3 (50) | 15 |
| Ellume | N protein, N.A., LF | 103.80 TCID$_{50}$/mL | 97 (148)/ 95 (40) | 20 |
| CareStart | N protein, LF, N.A. | 8 × 10^2 TCID/mL | 99.32 (149)/ 93.75 (31) | 10 |
| Repurpose Glucometer | S/N proteins, aptamer, N.A., Glucometer | 6.31 [S]/ 5.27 [N] pM protein | 100 (8)/ 100 (16) | 60 |
| Sofia 2 | N protein, LF, FL, N.A. | 113 TCID$_{50}$/ml | 100 (179)/ 96 (30) | 15 |
| LumiraDx | N protein, FLI, N.A. | 32 TCID$_{50}$/ml | 96.6 (174)/ 97.6 (83) | 12 |

Analysis of sensor specificity. The specificity of the disclosed sensor embodiments with aptamer-S and -N were tested by using closely correlated cognate antigens of MERS-COV, SARS-COV and inactive MERS-COV virus. As seen in FIGS. 19A and 19B, the results clearly indicate that aptamer-S and N significantly differentiate the MERS-COV and the SARS virus protein (>20% increment of sensor response). However, the graphene FET was unable to significantly differentiate between SARS-CoV and CoV-2 proteins. It was observed that Aptamer-N sensor response (50%) was higher with all tested protein samples compare to Aptamer-S (35%) and may be ascribed to higher affinity of aptamer ($K_d$, 0.5 nM compared to $K_d$, 5.8 nM for Aptamer-S).

To further verify the specificity of aptamers, the scrambled aptamer-S and Aptamer-N (as shown in Table 2 below) were used and derivatized the graphene surface of the GFET. FIGS. 19C and 19D illustrate the relative response of the aptamers (Aptamer-S, and -N) and the respective scrambled aptamers (Aptamer-S, and -N) derivatized on GFET with inactive SARS-COV-2 virus in saliva diluted in PBS buffer. To further analyze the specificity of the Aptamer-S and -N derivatized chip in simulated biological condition, different equivalent dilutions of inactive SARS-COV-2 and MERS-COV in 10× v/v saliva in 1×PBS buffer were prepared. The concentration dependent analysis showed that all the dilutions of inactive MERS-COV samples showed less than 10% of sensor response (see FIGS. 19E and 19F). One of the reasons for a high sensor response with SARS-COV and SARS-COV-2 may be the high affinity of aptamer-S at RBD amino acid position 500, 437, and 506 containing Threonine (T), asparagine (N) and glutamine (Q) while low sensor response with MERS might be due to presence of different amino acid[4][18] while MERS-CoV contain different amino acid (alanine (A), lysine (K), and alanine (A)) at same position of RBD.

Limit of detection (LoD) and limit of quantification (LoQ). To analyze the LoD and LoQ of our aptamer-based sensor, a concentration dependent sensor response analysis was performed with inactive viruses in simulated biological conditions. Triplicate data was fitted using linear fit and the LoD and LoQ calculated following FDA statistical data analysis guidelines. The results (shown in FIGS. 20A and 20B) indicate a LoD with aptamer-S of 1.28 PFU/mL ($R^2$=0.98) and aptamer-N of 1.45 PFU/mL ($R^2$=0.99) with inactive virus in 10% v/v saliva and 1×PBS buffer at room temperature. The estimated LoQ was 3.89 PFU/mL and 4.39 PFU/mL for aptamer-S and -N, respectively. The test showed higher sensitivity (lower LoD) compared to the FDA approved antigen test (see Table 1 above). These results demonstrate the sensitivity of the aptamer based GFET sensor to detect SARS-COV-2 in biological fluids and provides the motivation for investigations with real patient samples.

Clinical sample collection and analysis. Based on the simulated biological sample analysis, it was observed that aptamer-S derivatized GFET showed high sensor response while aptamer-N response was smaller (FIGS. 19D and 20B). Therefore, the aptamer-S derivatized GFET was used for patient sample analysis. To validate the GFET sensor with related samples, single blind experiment was performed with 10 each negative and positive sample and confirmed, independently through RT-PCR (as shown in FIGS. 20C and 20D). Moreover, 10 double blind samples

TABLE 2

Nucleic acid sequences screened for embodiments of the disclosed technology

| Sequence (5'-3') | Ref. | SEQ ID NO |
|---|---|---|
| Aptamer-S:<br>CAGCACCGACCTTGTGCTTTGGGAGTGCTGGTCCAAGGGC<br>GTTAATGGACA | [1] | 1 |
| Aptamer-S1:<br>ATCCAGAGTGACGCAGCATTTCATCGGGTCCAAAAGGGGC<br>TGCTCGGGATTGCGGATATGGACACGT | [1] | 2 |
| Aptamer-N:<br>GCTGGATGTCGCTTACGACAATATTCCTTAGGGGCACCGC<br>TACATTGACACATCCAGC | [2] | 3 |
| Aptamer-N1:<br>GCTGGATGTCACCGGATTGTCGGACATCGGATTGTCTGAG<br>TCATATGACACATCCAGC | [2] | 4 |
| Aptamer-N2:<br>GGGAGAGCGGAAGCGUGCUGGGCCUGUCGUUCGCUGUGUC<br>UUGCUACGUUACGUUACACGGUUGGCAUAACCCAGAGGUC<br>GAUGG | [3] | 5 |
| Aptamer-N3:<br>GGGAGAGCGGAAGCGUGCUGGGCCUCAUUACACACAUCUC<br>ACGGGAGACAUAGCUGACGAUAUCCAUAACCCAGAGGUCG<br>AUGG | [3] | 6 |
| Scrambled Aptamer-S:<br>GGTGGTTTGACTGATCAGAGACTATGCAGCTCTGGCCCGC<br>TAGCCGGAAGT | | 7 |
| Scrambled Aptamer-N:<br>TAGGTATATGTACGCACACCTAAGTCAGCTTGCCCGACGC<br>TGCAGCTCACATGTATGC | | 8 |

These results signify that both (Aptamer-S and -N) functionalized sensors are specific for SARS-COV-2 proteins in the virus. However, GFET sensor with aptamer-S showed higher sensor response compared to aptamer-N in simulated biological samples. Although earlier we have observed that it showed higher sensor response with cognate N-protein (see FIGS. 19A and 19B). Generally, the surface S-protein is more easily accessible compared to N-protein which is encapsulated within a lipid membrane[19].

were tested to confirm the test. Based on the results, the RT-PCR negative sample was used to predict with confidence interval (CI) of 99.7%+3σ of sensor response, which yields 132.6 mV of the $V_D$ shift (<20% of sensor response) for the samples. A threshold value of 132.6 mV was set with a $V_D$ shift above this threshold being considered as positive confirmation of SARS-COV-2 infection (see FIGS. 20C and 20D).

Figure 21A:
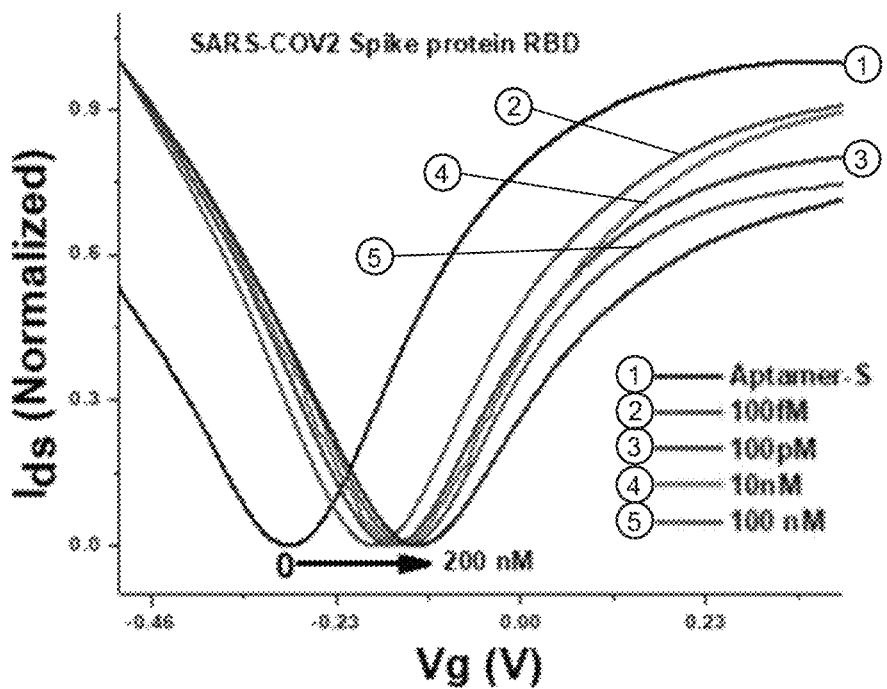
FIGS. 21A and 21B show examples of the mediated transfer curve analysis of the aptamer derivatized graphene FET.
Figure 21B:
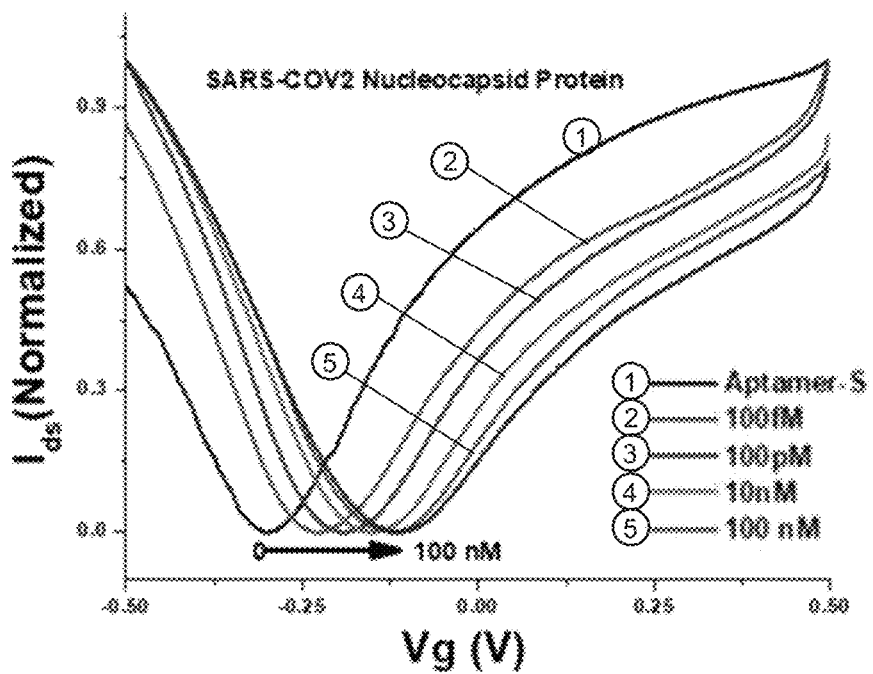
Figure 23A:
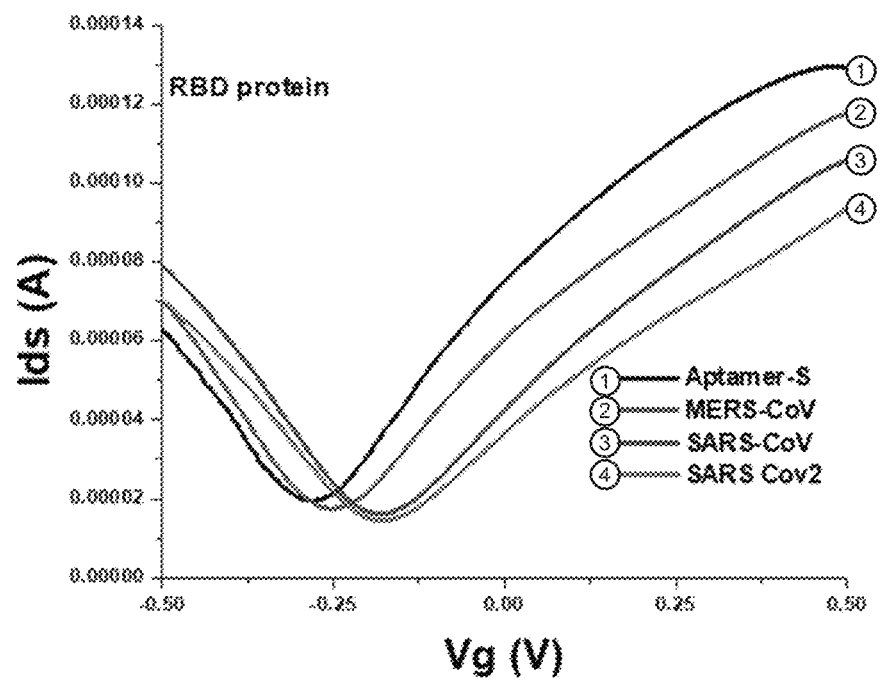
FIGS. 23A and 23B show example results from analyzing the specificity of the aptamer derivatized graphene FET.
Figure 23B:
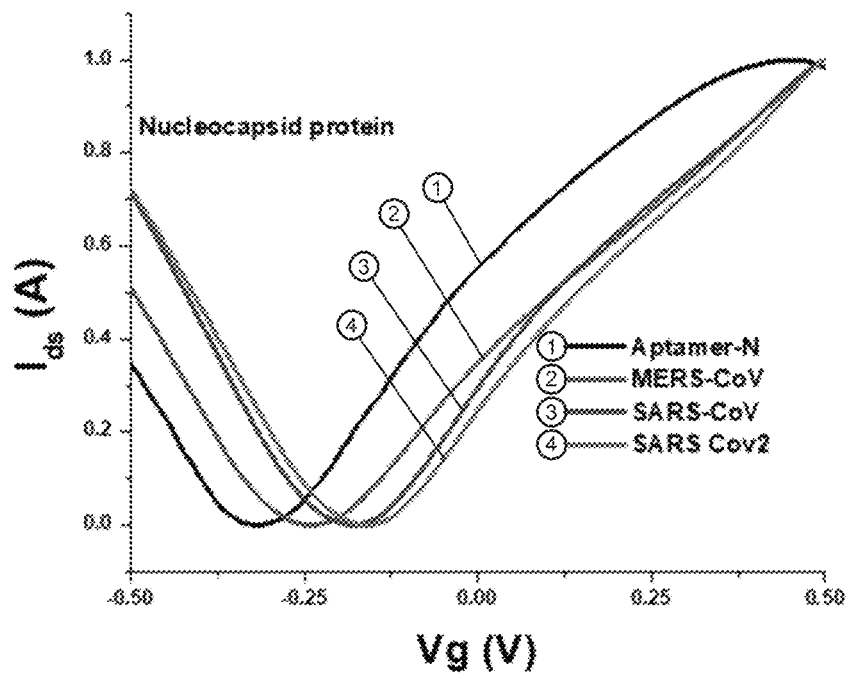

The efficacy of the disclosed technology is further evidenced in FIG. 21A that shows an example of SARS-COV-2 RBD binding mediated transfer curve analysis of Aptamer-S derivatized GFET, FIG. 21B that shows an example of SARS-COV-2 nucleocapsid protein binding mediated transfer curve analysis of Aptamer-N derivatized GFET, FIGS. 22A-22D that show examples of detecting the SARS-COV-2 RBD cognate protein of mutant N501Y, Y453F, D614G, and original virus, respectively, FIGS. 23A and 23B that show examples of analyzing the specificity of the Aptamer-S and Aptamer-N derivatized GFET, respectively, and Tables 3-6 shown below.

TABLE 3

Negative Saliva Sample Test Results (SARS-CoV-2 virus clinical testing)

| Sample Number | RTPCR Recorded | Ct Mean | PIVOT Biosensor Dirac Voltage Reading |
|---|---|---|---|
| N01 | Negative | >40 | −10.30 |
| N02 | Negative | >40 | −7.20 |
| N03 | Negative | >40 | 21.23 |
| N04 | Negative | >40 | 29.50 |
| N05 | Negative | >40 | 31.28 |
| N06 | Negative | >40 | 35.05 |
| N07 | Negative | >40 | 35.20 |
| N08 | Negative | >40 | 46.20 |
| N09 | Negative | >40 | 89.70 |
| N10 | Negative | >40 | 91.30 |
| Mean PIVOT Biosensor Dirac Voltage Mean for negative samples | | | 36.20 |
| Standard Deviation | | | 33.89 |
| 99.7% (3x Standard Deviation) Confidence Internal Upper Limit | | | 101.68 |
| Baseline for SARS-CoV-2 detection (PIVOT Biosensor readings above this value indicate SARS-CoV-2 virus present in sample) | | | 137.88 |

TABLE 4

Positive Saliva Sample Test Results (SARS-CoV-2 virus clinical testing)

| Sample Number | RTPCR Recorded | Ct Mean | PIVOT Biosensor Dirac Voltage Reading | PIVOT Biosensor Prediction (>137.88 Dirac voltage) |
|---|---|---|---|---|
| P01 | Positive | 18.37 | 217.19 | Positive |
| P02 | Positive | 24.35 | 205.80 | Positive |
| P03 | Positive | 24.70 | 247.85 | Positive |
| P04 | Positive | 24.92 | 204.88 | Positive |
| P05 | Positive | 26.19 | 136.10 | Positive |
| P06 | Positive | 28.08 | 532.68 | Positive |
| P07 | Positive | 28.70 | 145.60 | Positive |
| P08 | Positive | 30.96 | 163.29 | Positive |
| P09 | Positive | 32.14 | 149.55 | Positive |
| P10 | Positive | 32.60 | 226.60 | Positive |

TABLE 5

Blind Saliva Sample Test Results (SARS-CoV-2 virus clinical testing)

| Sample Number | PIVOT Biosensor Dirac voltage Reading | PIVOT Biosensor Prediction (>137.88 Dirac voltage) | RTPCR Recorded | Ct Mean |
|---|---|---|---|---|
| B01 | 102.11 | Negative | Negative | >40 |
| B02 | 83.20 | Negative | Negative | >40 |
| B03 | 68.80 | Negative | Negative | >40 |
| B04 | 127.90 | Negative | Negative | >40 |
| B05 | 217.57 | Positive | Positive | 20.92 |
| B06 | 461.11 | Positive | Positive | 22.80 |
| B07 | 205.80 | Positive | Positive | 24.35 |
| B08 | 199.71 | Positive | Positive | 27.46 |
| B09 | 348.02 | Positive | Positive | 29.63 |
| B10 | 175.97 | Positive | Positive | 27.67 |

TABLE 6

SARS-CoV-2-Delta/Omicron variant clinical test results

| Sample # | Aptamer | PIVOT Biosensor Dirac Voltage Reading | PIVOT Biosensor prediction | RT-PCR result | Ct # |
|---|---|---|---|---|---|
| 38 | N | 20.08 | Negative | Negative | 0 (>40) |
| 41 | S | 9.11 | Negative | Negative | 0 (>40) |
| 51 | S | 1.36 | Negative | Negative | 0 (>40) |
| 59 | N | 8.80 | Negative | Negative | 0 (>40) |
| 60 | N | 7.31 | Negative | Negative | 0 (>40) |
| 68 | N | 17.24 | Negative | Negative | 0 (>40) |
| 44 | S | 110.18 | Positive | Positive | 27.97 |
| 65 | N | 136.31 | Positive | Positive | 29.93 |
| 77 | N | 124.27 | Positive | Positive | 27.58 |
| 43 | S | 39.28 | Positive | Positive | 25.48 |

Figure 24A:
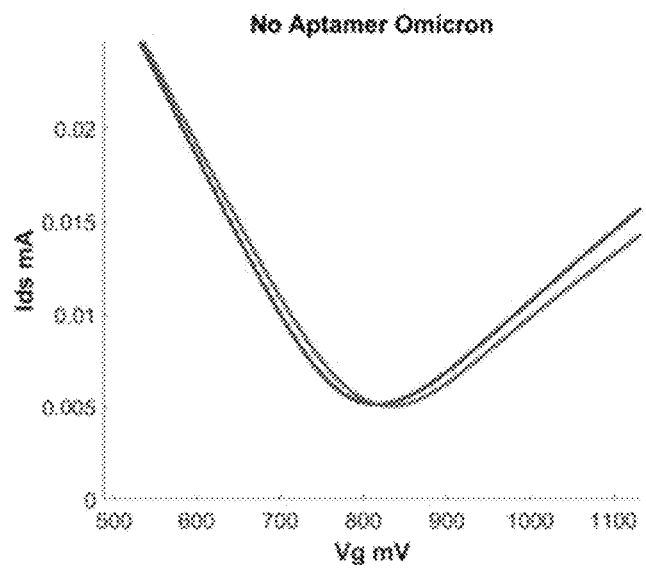
FIGS. 24A-24G show example results for the current-to-voltage (I-V) relationship of aptamer-anylate interactions.
Figure 24B:
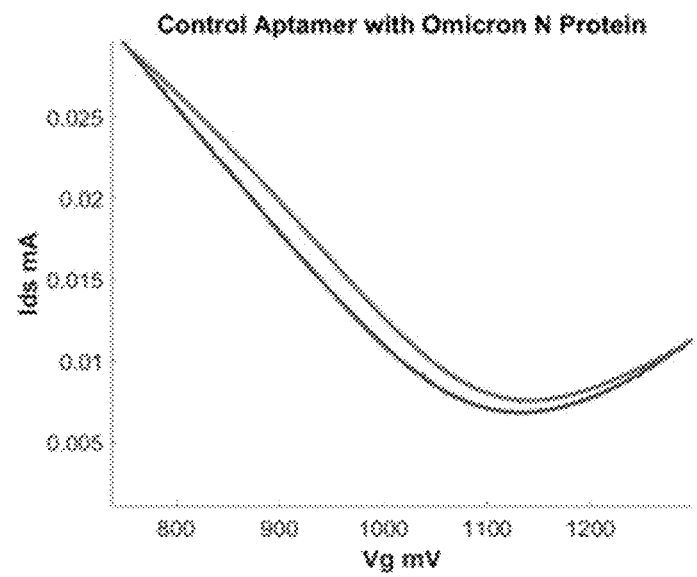
Figure 24C:
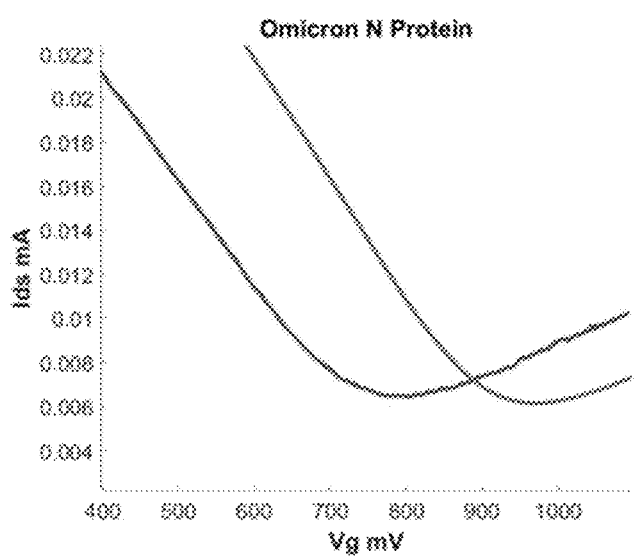

Example results for the current-to-voltage (I-V) relationship of aptamer-anylate interactions are shown in FIGS. 24A-24G. FIG. 24A shows that, in the absence of the aptamer on the GFET, there is no change in the Dirac potential shift, which motivates the need for the aptamer for sensing. The specificity of aptamer-omicron nucleocapsid protein binding is shown in FIG. 24B, in which the Dirac potential is negligible when a scrambled (or control) aptamer is used. The significant shift in Dirac potential is seen in FIG. 24C, which shows the effect of a specific interaction of aptamer-omicron nucleocapsid protein. The results in FIGS. 24A-24C are leveraged in the analyses of the results shown in FIGS. 24E-24G because currently there is no inactivated omicorn virus available.

Figure 24D:
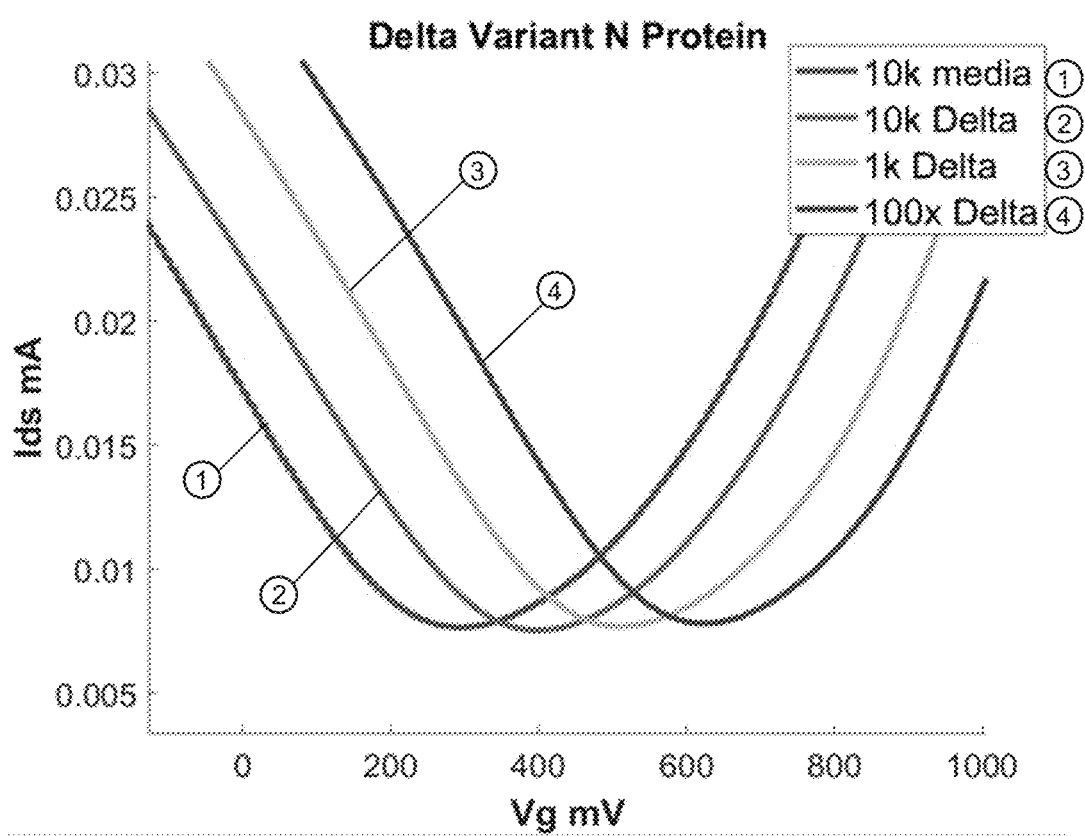

FIG. 24D shows a dose response I-V plot of an aptamer for various concentrations of inactivated Delta variant virus. The results in FIG. 24D are used to detect Delta variants in clinical samples, e.g., the example results shown in FIGS. 24E-24G. As discussed in this document, the disclosed embodiments can detect as few as 5-10 viruses.

Figure 24E:
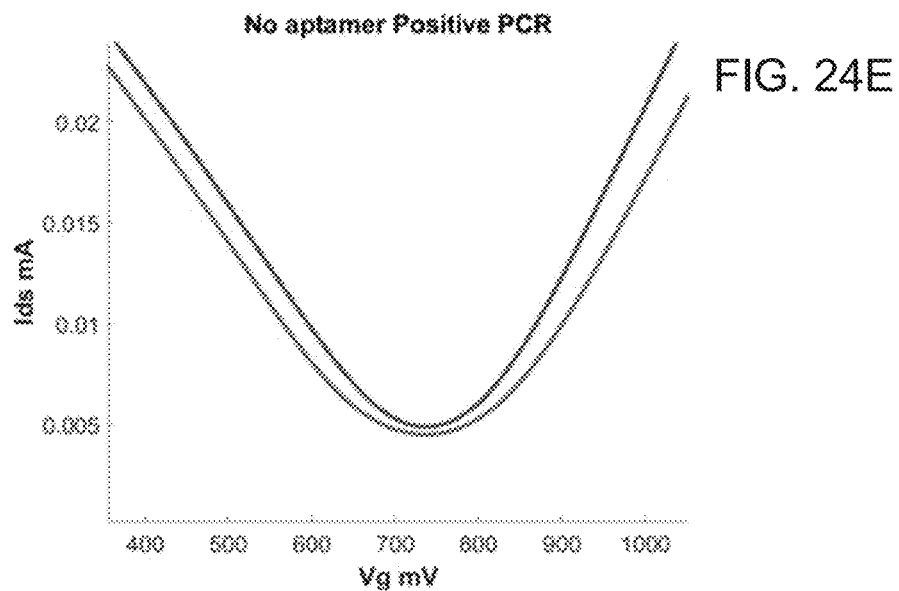
Figure 24F:
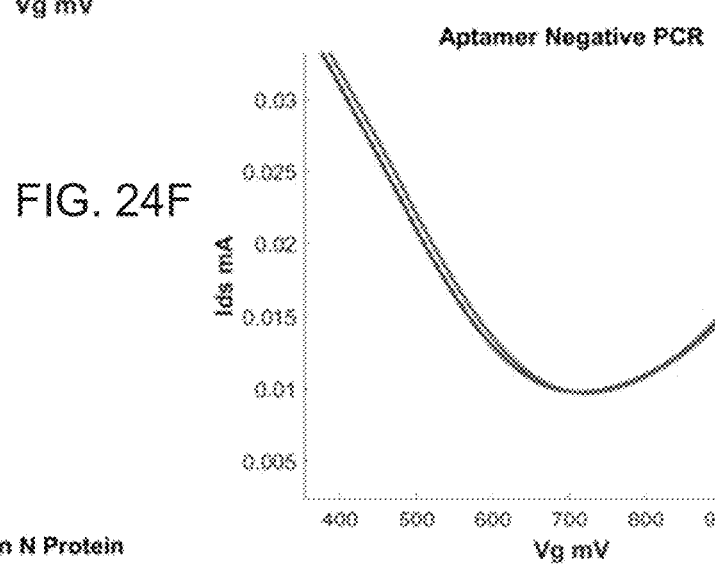
Figure 24G:
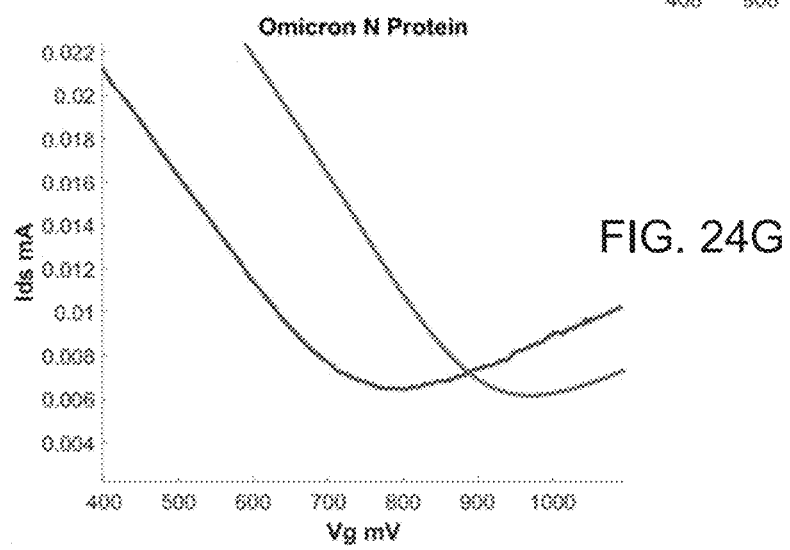

FIGS. 24E-24G show example results that include representative I-V curves for clinical testing in December 2021. As shown therein, in the absence of the aptamer (sensor), there is no to little change in the Dirac potential for both an individual whose RT-PCR tested positive (FIG. 24E) and an individual whose RT-PCR tested negative (FIG. 24F). However, for an RT-PCR positive individual (who is asymptomatic), there is a significant shift in the Dirac potential when the aptamer is present (FIG. 24G).

Figure 25A:
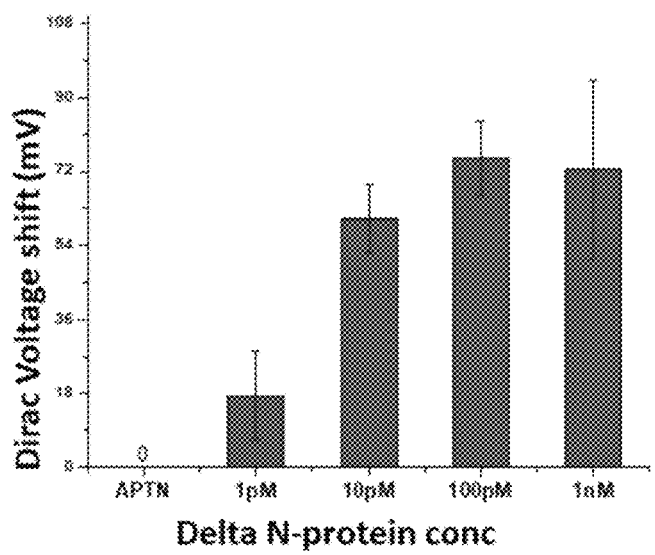
FIGS. 25A-25C shows example GFET device responses to the Delta variant N-protein, the Omicron variant N-protein, and the inactivated Delta variant, respectively.
Figure 25B:
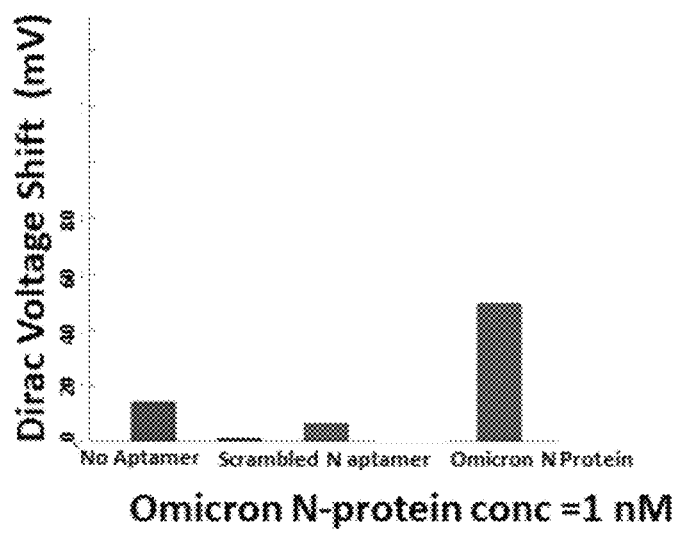
Figure 25C:
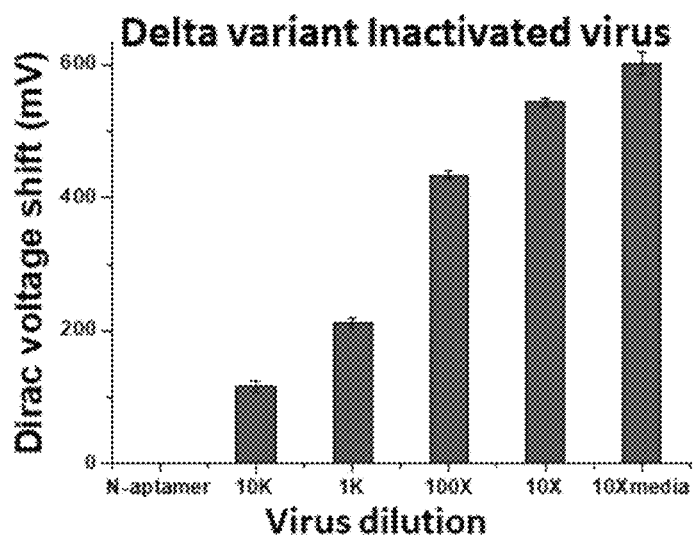

FIGS. 25A-25C shows example GFET device responses to the Delta variant N-protein, the Omicron variant N-protein, and the inactivated Delta variant virus, respectively. The results shown in FIGS. 25A and 25C were obtained using a method of serial dilution to determine the dose response of the GFET system for detecting the Delta variant. The GFET sensors were functionalized using the N-aptamer. Nucleocapsid protein (N-protein) ($2\text{-}4\times10^9$ copy/ml of ORF1a) of the Delta variant SARS-COV-2 (B.1.617.2) were tested. The various dilutions were tested serially on the PIVOT device using a single detection chip. The results shown in FIG. 25B were obtained using different detection chips, and each bar in FIG. 25C shows the shift from the baseline reading in saline to the viral omicron N-protein application of 10 µM. The control experiments included detection chips that were not functionalized with any aptamers (the "No Aptamer" bar in FIG. 25C) or functionalized with a control aptamer (e.g., a random sequence; the "scrambled N aptamer" bar in FIG. 25C).

Figure 26A:
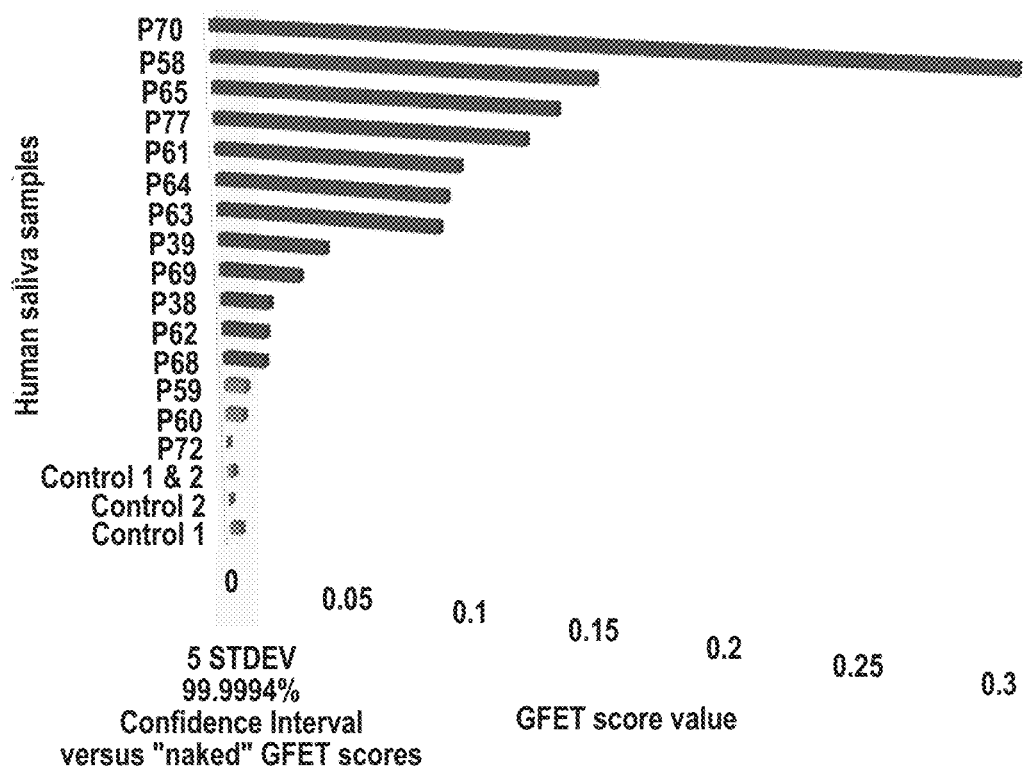
FIGS. 26A and 26B show example detection results of human saliva samples during the January 2022 Omicron wave using embodiments of the disclosed technology.
Figure 26B:
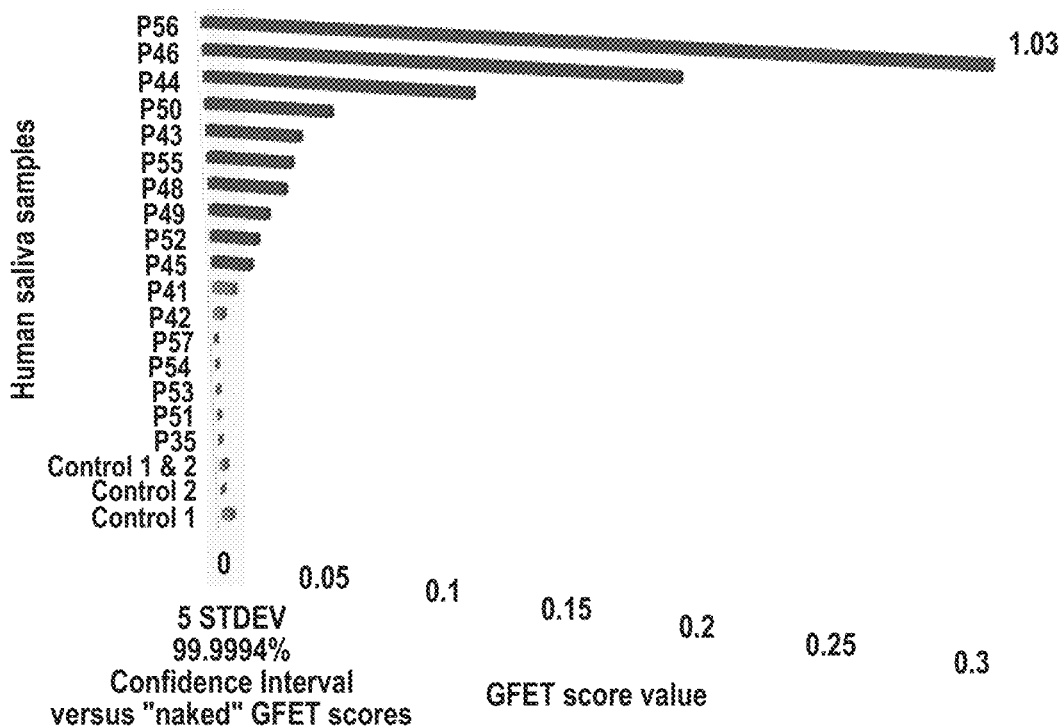

FIGS. 26A and 26B show example detection results of human saliva samples during the January 2022 Omicron wave for the N-aptamer and S-aptamer, respectively, using embodiments of the disclosed technology. As shown in FIG. 26A, a total of 15 samples were analyzed using N-aptamer GFET devices, of which 12 samples resulted in a positive score (indicating an Omicron infection), yielding an estimated 80% infection rate in the US. Similarly, as shown in FIG. 26B, a total of 17 samples were analyzed using S-aptamer GFET devices, of which 10 samples resulted in a positive score (indicating an Omicron infection), yielding an estimated 59% infection rate in the US. In combination, 32 samples were analyzed using either N- or S-aptamer GFET devices, of which 22 samples resulted in a positive score, yielding an estimated 69% infection rate in the US population.

Compared with available diagnostic devices on the market, the biosensor device of the current technology is cheaper (~$10/test), faster (~10 mins) and represents a portable point-of-care (POC) system with universal utility for current COVID-19 epidemic. The device also has the potential to be adapted for fast and precise detection of other coronaviruses (e.g., MERS-COV, SARS-COV), as well as mutants and/or variants of the viruses with little modification. It requires non-technical operation and allows rapid transmission of results to doctors, administrators, and public health individuals, contributing to the efforts in combating current and future pandemics.

Embodiments and Implementations of the Disclosed Technology

The disclosed technology includes devices biosensor devices for detecting one or more pathogens. In an example, the biosensor device includes a detection chip, which includes (a) a substrate with a graphene surface, (b) a conducting material at a first end and a second end of the graphene surface that form a first electrode and a second electrode, respectively, and (c) an insulating material to insulate the first electrode and the second electrode. In this example, one or more probes, which are attached to the graphene surface, specifically bind to one or more target molecules of the one or more pathogens. Furthermore, the insulating material forms a well to receive a biological sample such that the biological sample is in contact with the one or more probes. The biosensor device is shown, for example, in FIGS. 1B, 2B, 3 and 6.

In some embodiments, at least one of the one or more probes is an aptamer.

In some embodiments, the aptamer comprises a nucleic acid or a peptide. In some examples, the nucleic acid aptamer is selected from Table 2. In other examples, the nucleic acid is double-stranded. In yet other examples, the nucleic acid is single-stranded.

In some embodiments, the one or more pathogens are one or more variants of a coronavirus. In some examples, the one or more variants of the coronavirus include SARS-COV, SARS-COV-2, and MERS-COV.

In some embodiments, the target molecule is a nucleic acid or a protein.

In some embodiments, the target molecule includes an S protein of SARS-CoV-2, an N protein of SARS-COV-2, a variant thereof, or a subunit thereof.

In some embodiments, the one or more probes comprise multiple probes that are attached to different portions of the graphene surface. In some examples, a single detection chip, e.g., as shown in FIG. 1B, 2B, 3 or 6, can be configured to detect multiple pathogens using the multiple probes that are attached to the graphene surface of the GFET of the detection chip. This advantageously enables the described embodiments to be used in environmental monitoring and in global security applications.

In some embodiments, a first probe of the multiple probes is attached to a first portion of the graphene surface, and a second probe of the multiple probes is attached to a second portion of the graphene surface that is non-overlapping with the first portion. In some examples, the multiple probes specifically bind to different target molecules of a same pathogen. In other examples, the multiple probes specifically bind to different target molecules of different pathogens.

In some embodiments, the biosensor device further includes a plurality of detection chips comprising the detection chip, and each of the multiple probes is attached to a corresponding detection chip of the plurality of detection chips. In this embodiment, the described detection chips can be implemented as an array, which enables its deployment in environmental monitoring and global security applications, but also allows the plurality of detection chips to be processed simultaneously.

In some embodiments, a handheld device, e.g., as shown in FIGS. 13A and 13B, is configured to receive the biosensor device. In some examples, the handheld device is configured to perform a detection of the one or more pathogens based on the one or more probes specifically binding to the one or more target molecules of the one or more pathogens. In some examples, the handheld device comprises a wireless transceiver that is configured to transmit a result of the detection. The wireless transceiver may support at least one of a Bluetooth protocol, a Wi-Fi protocol, or a cellular protocol.

In some embodiments, the handheld device includes a power source, one or more visual indicators, coupled to the power source, configured to indicate a start and a completion of the detection of the one or more pathogens, and a display, coupled to the power source, to present a result of the detection for each of the one or more pathogens. In some examples, the one or more visual indicators comprise LEDs, the display comprises an LCD, and the power source comprises one or more batteries.

Embodiments of the disclosed technology also provide a method of detecting the presence of the one or more pathogens in the biological sample obtained from a subject. The method includes contacting the biological sample with the biosensor device described in any of the embodiments or implementations above.

In some embodiments, the biological sample comprises saliva, exhaled breath, nasal swab, or nasopharyngeal swab of the subject.

In some embodiments, a presence of less than 10 particles of the pathogen in the biological sample is detected.

Embodiments of the disclosed technology support inter alia the following technical solutions that solve the technical problem of accurately detecting one or more pathogens using a reliable, inexpensive, and portable device.

1. A biosensor device for detecting one or more pathogens, comprising a detection chip, comprising a substrate with a graphene surface, a conducting material at a first end and a second end of the graphene surface that form a first electrode and a second electrode, respectively, and an insulating material to insulate the first electrode and the second electrode, wherein one or more probes are attached to the graphene surface, wherein the one or more probes specifically bind to one or more target molecules of the one or more pathogens, and wherein the insulating material forms a well to receive a biological sample such that the biological sample is in contact with the one or more probes.

2. The biosensor of solution 1, wherein at least one of the one or more probes is an aptamer.

3. The biosensor of solution 2, wherein the aptamer comprises a nucleic acid or a peptide.

4. The biosensor of solution 3, wherein the nucleic acid is double-stranded.

5. The biosensor of solution 3, wherein the nucleic acid is single-stranded.

6. The biosensor of any one of solutions 1 to 5, wherein the one or more pathogens are one or more variants of a coronavirus.

7. The biosensor of solution 6, wherein the one or more variants of the coronavirus include SARS-COV, SARS-COV-2, and MERS-COV.

8. The biosensor of any one of solutions 1 to 7, wherein the target molecule is a nucleic acid or a protein.

9. The biosensor of any one of solutions 1 to 8, wherein the target molecule includes an S protein of SARS-COV-2, an N protein of SARS-COV-2, a variant thereof, or a subunit thereof.

10. The biosensor of any one of solutions 1 to 9, wherein the one or more probes comprise multiple probes that are attached to different portions of the graphene surface.

11. The biosensor of solution 10, wherein a first probe of the multiple probes is attached to a first portion of the graphene surface, and wherein a second probe of the multiple probes is attached to a second portion of the graphene surface that is non-overlapping with the first portion.

12. The biosensor of solution 10 or 11, wherein the multiple probes specifically bind to different target molecules of a same pathogen.

13. The biosensor of solution 10 or 11, wherein the multiple probes specifically bind to different target molecules of different pathogens.

14. The biosensor of solution 10, comprising a plurality of detection chips comprising the detection chip, wherein each of the multiple probes is attached to a corresponding detection chip of the plurality of detection chips.

15. The biosensor of any one of solutions 1 to 14, wherein a handheld device is configured to receive the biosensor device, and wherein the handheld device is configured to perform a detection of the one or more pathogens based on the one or more probes specifically binding to the one or more target molecules of the one or more pathogens.

16. The biosensor of solution 15, wherein the handheld device comprises a wireless transceiver that is configured to transmit a result of the detection.

17. The biosensor of solution 16, wherein the wireless transceiver supports at least one of a Bluetooth protocol, a Wi-Fi protocol, or a cellular protocol.

18. The biosensor of solution 15, wherein the handheld device comprises a power source, one or more visual indicators, coupled to the power source, configured to indicate a start and a completion of the detection of the one or more pathogens, and a display, coupled to the power source, to present a result of the detection for each of the one or more pathogens.

19. The biosensor of solution 18, wherein the one or more visual indicators comprise light-emitting diodes (LEDs), the display comprises a liquid crystal display (LCD), and the power source comprises one or more batteries.

20. A method of detecting the presence of the one or more pathogens in a biological sample obtained from a subject, the method comprising contacting the biological sample with the biosensor device of any one of solutions 1 to 19.

21. The method of solution 20, wherein the biological sample is selected from the group consisting of saliva, exhaled breath, nasal swab, or nasopharyngeal swab of the subject.

22. The method of solution 20 or 21, wherein a presence of less than 10 particles of the pathogen in the biological sample is detected.

23. A method of environmental monitoring, comprising collecting a sample selected from the group consisting of a soil sample, an aerosol sample, an air sample, or a water sample, contacting the sample with the biosensor device of any one of solutions 1 to 19, and detecting the presence of the one or more pathogens in the at least one sample.

24. The method of solution 23, wherein the one or more pathogens comprise one or more of a heavy metal, a small-molecule agricultural toxin, a water-borne bacterial pathogen, an aquatic toxin, a pesticide, an industrial byproduct, an antibiotics, or a pharmaceutical.

REFERENCES

[1] S. Khan, A. Ali, H. Shi, R. Siddique, G. Nabi, J. Hu, T. Wang, M. Dong, W. Zaman, G. Han, *Saudi Pharmaceutical Journal* 2020, 28, 1004.
[2] R. de Oliveira Andrade, *bmj* 2020, 370.
[3] M. Sorbello, K. El-Boghdadly, I. Di Giacinto, R. Cataldo, C. Esposito, S. Falcetta, G. Merli, G. Cortese, R. Corso, F. Bressan, *Anaesthesia* 2020, 75, 724.
[4] Y. Song, J. Song, X. Wei, M. Huang, M. Sun, L. Zhu, B. Lin, H. Shen, Z. Zhu, C. Yang, *Analytical Chemistry* 2020, 92, 9895.
[5] L. Zhang, X. Fang, X. Liu, H. Ou, H. Zhang, J. Wang, Q. Li, H. Cheng, W. Zhang, Z. Luo, *Chemical Communications* 2020, 56, 10235.
[6] Z. Daniloski, T. X. Jordan, J. K. Ilmain, X. Guo, G. Bhabha, B. R. tenOever, N. E. Sanjana, *eLife* 2021, 10, e65365.
[7] L. Zhang, C. B. Jackson, H. Mou, A. Ojha, E. S. Rangarajan, T. Izard, M. Farzan, H. Choe, *bioRxiv* 2020, 2020.06.12.148726.
[8] J. A. Plante, Y. Liu, J. Liu, H. Xia, B. A. Johnson, K. G. Lokugamage, X. Zhang, A. E. Muruato, J. Zou, C. R. Fontes-Garfias, D. Mirchandani, D. Scharton, J. P. Bilello, Z. Ku, Z. An, B. Kalveram, A. N. Freiberg, V. D. Menachery, X. Xie, K. S. Plante, S. C. Weaver, P.-Y. Shi, *Nature* 2021, 592, 116.

[9] Z. Ding, X. Liu, X. Ren, Q. Zhang, T. Zhang, Q. Qian, W. Liu, C. Jiang, *Discovery medicine* 2016, 21, 331.
[10] US Food and Drug Administration, US FDA, *Silver Spring*, MD 2007.
[11] N. R. Pollock, T. J. Savage, H. Wardell, R. Lee, A. Mathew, M. Stengelin, G. B. Sigal, *medRxiv* 2020, 2020.11.10.20227371.
[12] Y. Pan, D. Zhang, P. Yang, L. L. M. Poon, Q. Wang, *Lancet Infect Dis* 2020, 20, 411.
[13] A. D. Winder, A. S. Mora, E. Berry, J. R. Lurain, *Gynecol Oncol Rep* 2017, 21, 34.
[14] G. M. S. Ross, D. Filippini, M. W. F. Nielen, G. I J. Salentijn, *Anal. Chem.* 2020, 92, 15587.
[15] W. F. Garcia-Beltran, E. C. Lam, K. S. Denis, A. D. Nitido, Z. H. Garcia, B. M. Hauser, J. Feldman, M. N. Pavlovic, D. J. Gregory, M. C. Poznansky, *Cell* 2021, 184, 2372.
[16] U. FDA, n.d.
[17] S. Guo, K. Liu, J. Zheng, *Int J Biol Sci* 2021, 17, 1476.
[18] W. Tai, L. He, X. Zhang, J. Pu, D. Voronin, S. Jiang, Y. Zhou, L. Du, *Cellular & Molecular Immunology* 2020, 17, 613.
[19] M.-Y. Wang, R. Zhao, L.-J. Gao, X.-F. Gao, D.-P. Wang, J.-M. Cao, *Frontiers in Cellular and Infection Microbiology* 2020, 10, 724.

CONCLUSION

The above detailed description of embodiments of the technology are not intended to be exhaustive or to limit the technology to the precise forms disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known components and functions have not been shown or described in detail to avoid unnecessarily obscuring the description of the embodiments of the technology. Where the context permits, singular or plural terms may also include the plural or singular term, respectively. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

---

What is claimed is:

1. A system for detecting one or more pathogens, comprising:
   a biosensor device comprising a detection chip; and
   a handheld device configured to receive the biosensor device,
   the detection chip, comprising:
     a substrate comprising a graphene surface that is maintained at a fixed voltage,
     a conducting material at a first end and a second end of the graphene surface that form a first electrode and a second electrode, respectively, wherein the first electrode and the second electrode correspond to a source and a drain, respectively, and wherein the source and the drain are positioned in a same plane as a third electrode corresponding to an extended gate, and
     an insulating material to insulate the first electrode and the second electrode,
     wherein one or more probes are attached to the graphene surface,
     wherein the one or more probes specifically bind to one or more target molecules of the one or more pathogens, and
     wherein the insulating material forms a well to receive a biological sample such that the biological sample is in contact with the one or more probes and the graphene surface.

2. The system of claim 1, wherein at least one of the one or more probes is an aptamer.

3. The system of claim 2, wherein the aptamer is a peptide module or an oligonucleotide molecule that has been modified at its 3' end.

4. The system of claim 3, wherein the oligonucleotide molecule is double-stranded or single-stranded.

5. The system of claim 1, wherein the one or more pathogens are one or more variants of a coronavirus.

6. The system of claim 5, wherein the one or more variants of the coronavirus include SARS-COV, SARS-COV-2, and MERS-COV.

7. The system of claim 1, wherein the one or more target molecules includes a nucleic acid or a protein.

8. The system of claim 1, wherein the one or more target molecules includes an S protein of SARS-COV-2, an N protein of SARS-COV-2, a variant thereof, or a subunit thereof.

9. The system of claim 1, wherein the handheld device is configured to perform a detection of the one or more pathogens based on the one or more probes specifically binding to the one or more target molecules of the one or more pathogens.

10. The system of claim 9, wherein performing the detection comprises detecting a change in a resistance of the graphene surface caused by the one or more probes specifically binding to the one or more target molecules of the one or more pathogens.

11. The system of claim 10, wherein the change in the resistance of the graphene surface is indicative of a presence of the one or more target molecules, and wherein a magnitude of the change in the resistance of the graphene surface is indicative of a concentration of the one or more target molecules.

12. The system of claim 9, wherein the handheld device comprises a wireless transceiver that is configured to transmit a result of the detection, and wherein the wireless transceiver supports at least one of a Bluetooth protocol, a Wi-Fi protocol, or a cellular protocol.

13. The system of claim 9, wherein the handheld device comprises:
- a power source;
- one or more visual indicators, coupled to the power source, configured to indicate a start and a completion of the detection of the one or more pathogens; and
- a display, coupled to the power source, to present a result of the detection for each of the one or more pathogens.

14. The system of claim 1, wherein the biological sample comprises saliva, sweat, tears, exhaled breath, blood, urine, a nasal swab, a nasopharyngeal swab, or a fecal swab of a subject.

15. A method of detecting a presence of one or more pathogens in a biological sample, comprising:
- receiving, from a subject, the biological sample;
- contacting the biological sample with a biosensor device comprising a detection chip;
- inserting the biosensor device into a handheld device; and
- determining, using the handheld device, whether the one or more pathogens are present in the biological sample, wherein the detection chip comprises:
  - a substrate comprising a graphene surface that is maintained at a fixed voltage;
  - a conducting material at a first end and a second end of the graphene surface that form a first electrode and a second electrode, respectively, wherein the first electrode and the second electrode correspond to a source and a drain, respectively, and wherein the source and the drain are positioned in a same plane as a third electrode corresponding to an extended gate; and
  - an insulating material to insulate the first electrode and the second electrode,
  - wherein one or more probes are attached to the graphene surface,
  - wherein the one or more probes specifically bind to one or more target molecules of the one or more pathogens, and
  - wherein the insulating material forms a well to receive the biological sample such that the biological sample is in contact with the one or more probes and the graphene surface.

16. The method of claim 15, wherein determining that the one or more pathogens are present in the biological sample comprises:
- detecting a change in a resistance of the graphene surface caused by the one or more probes specifically binding to the one or more target molecules of the one or more pathogens.

17. The method of claim 16, wherein a magnitude of the change in the resistance of the graphene surface is indicative of a concentration of the one or more target molecules.

18. The method of claim 15, wherein the detection chip is a single-use chip.

19. The method of claim 15, wherein the one or more probes comprise a single stranded aptamer, and wherein the one or more target molecules comprise nucleic acid molecules or protein molecules.

20. The method of claim 15, wherein, upon determining that the one or more pathogens are present in the biological sample, the method further comprises:
- transmitting, using a wireless transmitter in the handheld device, one or more results of determining that the one or more pathogens are present in the biological sample to a computing device or a data storage device.

* * * * *